(12) United States Patent
Glasgow et al.

(10) Patent No.: US 11,944,146 B2
(45) Date of Patent: Apr. 2, 2024

(54) BODY MEASUREMENT GARMENT FOR OPTIMAL GARMENT FIT

(71) Applicant: eBay Inc., San Jose, CA (US)

(72) Inventors: Dane Glasgow, Los Altos, CA (US); David Ramadge, San Jose, CA (US); Matthew Bret MacLaurin, Santa Cruz, CA (US); Corinne Sherman Stewart, San Jose, CA (US); Timothy Carlson, Menlo Park, CA (US); Bria Selhorst, Albany, CA (US)

(73) Assignee: eBay Inc., San Jose, CA (US)

( * ) Notice: Subject to any disclaimer, the term of this patent is extended or adjusted under 35 U.S.C. 154(b) by 0 days.

(21) Appl. No.: 17/952,274

(22) Filed: Sep. 25, 2022

(65) Prior Publication Data

US 2023/0014892 A1 Jan. 19, 2023

Related U.S. Application Data

(63) Continuation of application No. 16/950,526, filed on Nov. 17, 2020, now Pat. No. 11,484,079, which is a (Continued)

(51) Int. Cl.
*A41H 1/02* (2006.01)
*G01B 21/20* (2006.01)
(Continued)

(52) U.S. Cl.
CPC ............. *A41H 1/02* (2013.01); *G01B 21/20* (2013.01); *G06Q 30/00* (2013.01);
(Continued)

(58) Field of Classification Search
CPC .... G06Q 30/0269; G06Q 30/00; G01B 21/20; A41H 1/02
(Continued)

(56) References Cited

U.S. PATENT DOCUMENTS 6,415,199 B1 7/2002 Liebermann
6,813,838 B2 11/2004 McCormick
(Continued)

FOREIGN PATENT DOCUMENTS

CN 102842089 12/2012
CN 103455501 12/2013
(Continued)

OTHER PUBLICATIONS

"Advisory Action", U.S. Appl. No. 14/568,187, dated Oct. 31, 2017, 3 pages.
(Continued)

*Primary Examiner* — Kesha Frisby
(74) *Attorney, Agent, or Firm* — FIG. 1 Patents

(57) ABSTRACT

A system comprising a machine-readable storage medium storing at least one program and a computer-implemented method for collecting body measurements of a human user using a body measurement garment is provided. The body measurement garment comprises a plurality of sensors configured to produce a set of output data. The method may include receiving the set of output data from the body measurement garment and determining a plurality of body measurements from the output data. The method may further include generating a body shape model representing the shape of the body of the user. The method may also include generating a garment fit model representing the fit of a garment on the human user.

20 Claims, 15 Drawing Sheets

Related U.S. Application Data continuation of application No. 16/190,362, filed on Nov. 14, 2018, now Pat. No. 10,869,515, which is a continuation of application No. 14/568,187, filed on Dec. 12, 2014, now Pat. No. 10,172,403.

(51) Int. Cl.
| | |
|---|---|
| *G06Q 30/00* | (2023.01) |
| *G06Q 30/0251* | (2023.01) |
| *A41D 1/00* | (2018.01) |
| *A61B 5/00* | (2006.01) |
| *A61B 5/107* | (2006.01) |

(52) U.S. Cl.
CPC ......... *G06Q 30/0269* (2013.01); *A41D 1/002* (2013.01); *A61B 5/1072* (2013.01); *A61B 5/6805* (2013.01)

(58) Field of Classification Search
USPC .......................................................... 703/11
See application file for complete search history.

(56) References Cited

U.S. PATENT DOCUMENTS

| | | | |
|---|---|---|---|
| 7,354,411 | B2 | 4/2008 | Perry et al. |
| 8,090,465 | B2 | 1/2012 | Zeng |
| 10,109,112 | B2 | 10/2018 | Glasgow et al. |
| 10,172,403 | B2 | 1/2019 | Glasgow et al. |
| 10,869,515 | B2 | 12/2020 | Glasgow et al. |
| 11,151,803 | B2 | 10/2021 | Glasgow et al. |
| 11,484,079 | B2 | 11/2022 | Glasgow |
| 2003/0139896 | A1 | 7/2003 | Dietz et al. |
| 2004/0227752 | A1 | 11/2004 | McCartha et al. |
| 2007/0198118 | A1 | 8/2007 | Lind |
| 2007/0214541 | A1 | 9/2007 | Kawasaki et al. |
| 2011/0063208 | A1 | 3/2011 | Van Den Eerenbeemd et al. |
| 2012/0078145 | A1 | 3/2012 | Malhi et al. |
| 2013/0071584 | A1 | 3/2013 | Bell |
| 2014/0121473 | A1 | 5/2014 | Banet et al. |
| 2014/0139353 | A1 | 5/2014 | Wojcieszak et al. |
| 2014/0176565 | A1 | 6/2014 | Adeyooia et al. |
| 2015/0134495 | A1 | 5/2015 | Naware et al. |
| 2015/0366504 | A1 | 12/2015 | Connor |
| 2016/0120733 | A1 | 5/2016 | Ishikawa et al. |
| 2016/0165988 | A1 | 6/2016 | Glasgow et al. |
| 2016/0165989 | A1 | 6/2016 | Glasgow et al. |
| 2019/0012845 | A1 | 1/2019 | Glasgow et al. |
| 2019/0075871 | A1 | 3/2019 | Glasgow et al. |
| 2021/0059340 | A1 | 3/2021 | Glasgow et al. |
| 2022/0005287 | A1 | 1/2022 | Glasgow et al. |

FOREIGN PATENT DOCUMENTS

| | | |
|---|---|---|
| KR | 201100040648 A | 4/2011 |
| WO | WO-2013188908 | 12/2013 |

OTHER PUBLICATIONS

"Examiner Interview Summary", U.S. Appl. No. 14/569,197, dated Apr. 28, 2017, 2 pages.
"Final Office Action", U.S. Appl. No. 14/569,197, dated Nov. 3, 2017, 12 pages.
"Final Office Action", U.S. Appl. No. 14/568,187, dated Aug. 16, 2017, 13 pages.
"First Action Interview Office Action", U.S. Appl. No. 14/569,197, dated Jun. 1, 2017, 4 pages.
"First Action Interview Office Action", U.S. Appl. No. 14/568,187, dated Mar. 13, 2017, 5 pages.
"Non-Final Office Action", U.S. Appl. No. 14/568,187, dated Jan. 12, 2018, 15 pages.
"Preinterview First Office Action", U.S. Appl. No. 14/568,187, dated Oct. 6, 2016, 4 pages.
"Preinterview First Office Action", U.S. Appl. No. 14/569,197, dated Oct. 11, 2016, 4 pages.
U.S. Appl. No. 14/568,187, , "Amendment After 312 received for U.S. Appl. No. 14/568,187, dated Oct. 31, 2017", dated Oct. 31, 2017, 1 Page.
U.S. Appl. No. 14/568,187, , "Applicant Initiated Interview Request filed for U.S. Appl. No. 14/568,187 , dated Oct. 31, 2016", dated Oct. 31, 2016, 1 Page.
U.S. Appl. No. 14/568,187, , "Applicant Initiated Interview Summary received for U.S. Appl. No. 14/568,187 , dated Mar. 13, 2017", dated Mar. 13, 2017, 2 Pages.
U.S. Appl. No. 14/568,187, , "Notice of allowance received for U.S. Appl. No. 14/568,187, dated Aug. 10, 2018", dated Aug. 10, 2018, 7 Pages.
U.S. Appl. No. 14/568,187, , "Notice of Allowance received for U.S. Appl. No. 14/568,187, dated Dec. 18, 2018", dated Dec. 18, 2018, 2 Pages.
U.S. Appl. No. 14/569,197, , "Advisory Action received for U.S. Appl. No. 14/569,197, dated Feb. 2, 2018", dated Feb. 2, 2018, 3 Pages.
U.S. Appl. No. 14/569,197, , "Amendment after 312 Initiated by Examiner filed for U.S. Appl. No. 14/569,197, dated Feb. 2, 2018", dated Feb. 2, 2018, 1 Page.
U.S. Appl. No. 14/569,197, , "Applicant Initiated Interview Request filed for U.S. Appl. No. 14/569,197 , dated Oct. 31, 2016", dated Oct. 31, 2016, 1 Page.
U.S. Appl. No. 14/569,197, , "Corrected Notice of Allowability received for U.S. Appl. No. 14/569,197, dated Jul. 18, 2018", dated Jul. 18, 2018, 2 Pages.
U.S. Appl. No. 14/569,197, , "Corrected Notice of Allowability received for U.S. Appl. No. 14/569,197, dated Sep. 26, 2018", dated Sep. 26, 2018, 2 Pages.
U.S. Appl. No. 14/569,197, , "Notice of Allowance received for U.S. Appl. No. 14/569,197 , dated Jun. 7, 2018", dated Jun. 7, 2018, 8 Pages.
U.S. Appl. No. 14/569,197, , "Notice of Allowance received for U.S. Appl. No. 14/569,197 , dated Sep. 26, 2018", dated Sep. 26, 2018, 2 Pages.
U.S. Appl. No. 16/128,829, , "Non Final Office Action Received for U.S. Appl. No. 16/128,829, dated Mar. 18, 2021", dated Mar. 18, 2021, 4 Pages.
U.S. Appl. No. 16/128,829, , "Notice Of Allowance received for U.S. Appl. No. 16/128,829, dated Jun. 18, 2021", dated Jun. 18, 2021, 7 Pages.
U.S. Appl. No. 16/190,362, , "Corrected Notice Of Allowance received for U.S. Appl. No. 16/190,362, dated Oct. 6, 2020", dated Oct. 6, 2020, 4 Pages.
U.S. Appl. No. 16/190,362, , "Notice Of Allowance received for U.S. Appl. No. 16/190,362, dated Oct. 2, 2020", dated Oct. 2, 2020, 7 Pages.
U.S. Appl. No. 16/950,526, , "Final Office Action received for U.S. Appl. No. 16/950,526, dated Apr. 14, 2022", dated Apr. 14, 2022, 8 pages.
U.S. Appl. No. 16/950,526, , "Non Final Office Action Received for U.S. Appl. No. 16/950,526, dated Feb. 2, 2022", dated Feb. 2, 2022, 8 Pages.
U.S. Appl. No. 16/950,526, , "Notice of Allowance", U.S. Appl. No. 16/950,526, dated Aug. 25, 2022, 7 pages.
Gioberto, Guido et al., "Garment-Integrated Wearable Sensing for Knee Joint Monitoring", Proceedings of the 2014 ACM International Symposium on Wearable Computers: Adjunct Program, Sep. 13, 2014, 6 pages.
Gioberto, Guido et al., "Overlock-Stitched Stretch Sensors: Characterization and Effect of Fabric Property", Journal of Textile and Apparel, Technology and Management, vol. 8, Issue 3, (Winter 2013),, Dec. 2013, 14 pages.
Li, Hongqiang et al., "Wearable Sensors in Intelligent Clothing for Measuring Human Body Temperature Based on Optical Fiber Bragg Grating", Optics Express, vol. 20 (11), [Online]. Retrieved from the Internet: <URL: htp://ro.uow.edu.au/eispapers/298>,, 050/9/2012, 13 Pages.
U.S. Appl. No. 17/479,576, "Non-Final Office Action", U.S. Appl. No. 17/479,576, dated Sep. 19, 2023, 12 pages.

(56) References Cited

OTHER PUBLICATIONS

U.S. Appl. No. 17/479,576, "Non-Final Office Action", U.S. Appl. No. 17/479,576, dated Jan. 16, 2024, 13 pages.

BODY MEASUREMENT GARMENT FOR OPTIMAL GARMENT FIT

CLAIM OF PRIORITY

This Application is a Continuation of U.S. application Ser. No. 16/950,526 filed Nov. 17, 2020, which is a Continuation of U.S. application Ser. No. 16/190,362, filed Nov. 14, 2018, which is a Continuation of U.S. application Ser. No. 14/568,187, filed Dec. 12, 2014, which are hereby incorporated by reference in their entirety.

TECHNICAL FIELD

This application relates to data processing. In particular, example embodiments relate to a garment for taking body measurements.

BACKGROUND

Most clothing sold online and at brick-and-mortar retail stores is made according to a standard sizing model. However, the actual shape and dimensions of clothing varies widely between clothing manufacturers, and often varies between different clothing lines provided by the same clothing manufacturer. Further, clothing sizing standards often vary from country to country. These sizing discrepancies leave consumers who wish to shop for clothing remotely—either online or using a telepresence robot—at a severe disadvantage. Even though clothing may be indicated to be of a certain size, without the actual clothing item within their physical presence, a consumer does not have enough information to discern how a particular item of clothing may actually look and feel when worn. Thus, consumers may be hesitant to shop for clothing remotely, or they may even avoid it all together.

BRIEF DESCRIPTION OF THE DRAWINGS

Various ones of the appended drawings merely illustrate example embodiments of the present disclosure and cannot be considered as limiting its scope.

DETAILED DESCRIPTION

Figure 1:
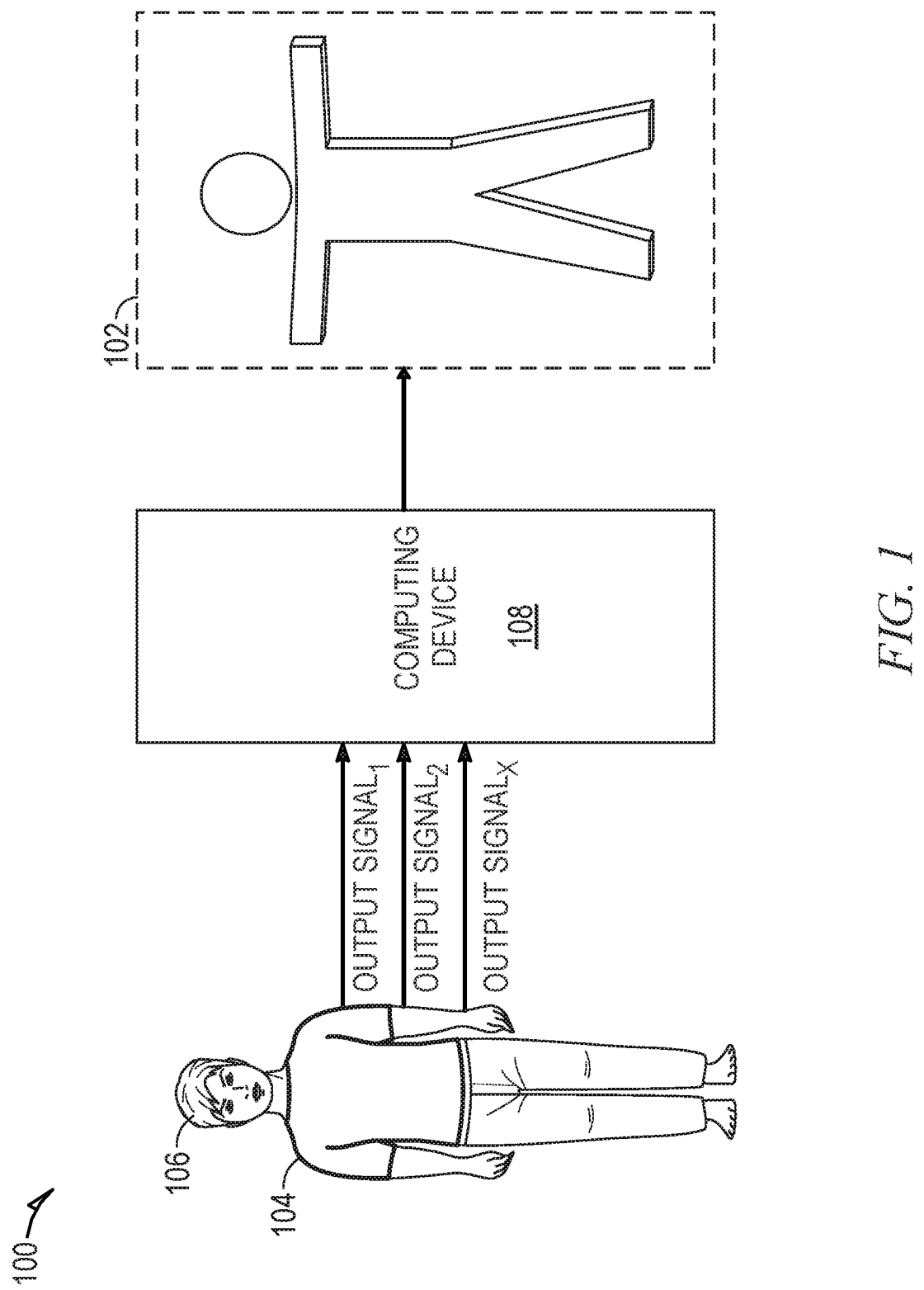
FIG. 1 is a context diagram illustrating a body measurement system configured to generate a body shape model using output from a body measurement garment, according to an example embodiment.

Reference will now be made in detail to specific example embodiments for carrying out the inventive subject matter. Examples of these specific embodiments are illustrated in the accompanying drawings. It will be understood that these examples are not intended to limit the scope of the claims to the illustrated embodiments. On the contrary, they are intended to cover alternatives, modifications, and equivalents as may be included within the scope of the disclosure. In the following description, specific details are set forth in order to provide a thorough understanding of the subject matter. Embodiments may be practiced without some or all of these specific details.

Aspects of the present disclosure involve systems and methods for determining body measurements of a human user using a body measurement garment. The body measurement garment includes a number of sensors to generate a number of outputs that correspond to body measurements of a user wearing the garment. As such, the body measurement garment may achieve the technical effect of increasing accuracy and precision of body measurements used in the manufacturing of clothing. Accordingly, the output from the garment may be utilized for a number of purposes including generating an electronic measurement profile of the user that may be shared with a clothing manufacturer to produce accurately measured bespoke or made-to-order clothing.

The measurement profile may also be used to generate a virtual representation of the user that can be used in online shopping contexts to provide the user with a view of how garments the user is shopping for may actually fit when worn by the user. The electronic measurement profile may also include user fit preferences that may be based on comments received by the user regarding the desired fit of garments. In some example embodiments, the output from the body measurement garment may be used to provide a model of a normal clothing wear pattern of the user.

Aspects of the present disclosure involve systems and methods for simulating fit of clothing on a user using a fit simulation garment. For purposes of this specification, the term "fit" refers to the particular manner in which a garment conforms to the shape of at least a portion of a human body.

The fit simulation garment is able to be worn by the user and may comprise a plurality of actuators that act to simulate the fit of a particular garment when worn by the user. The fit of the garment simulated by the fit simulation garment may include the tightness of the garment on the human body as well as the sensation caused by the fabric on the skin of the human body. The fit simulation garment may simulate the fit of a particular garment based on a garment fit model, which is a set of data that describes the fit of a particular garment on a user. Accordingly, example embodiments may involve generating a garment fit model based, in part, on an electronic measurement profile of the user and a garment model describing various aspects (e.g., shape, dimensions, fabric) of the particular garment.

Consistent with some embodiments, the fit simulation garment may simulate the fit of a garment based on output received from a personalized fitting mannequin, which is a physical, real-world, metrologically correct representation of a human user having embedded sensors to measure the tightness of a garment as it would be felt by the user. The personalized fitting mannequin may, for example, be utilized (e.g., in conjunction with a telepresence robot) in a brick-and-mortar retail setting to allow the user to shop remotely from items offered for sale by the brick-and-mortar retail store. By using the personalized fitting mannequin, the user is able to see how a particular garment actually looks when worn (e.g., through a video feed provided by the telepresence robot), while receiving the simulated feel of how the garment actually feels when worn.

FIG. 1 is a context diagram illustrating a body measurement system 100 configured to generate a body shape model 102 using output from a body measurement garment 104, according to an example embodiment. To avoid obscuring the inventive subject matter with unnecessary detail, various functional components (e.g., modules and engines) that are not germane to conveying an understanding of the inventive subject matter have been omitted from FIG. 1. However, a skilled artisan will readily recognize that various additional functional components may be supported by the body measurement system 100 to facilitate additional functionality that is not specifically described herein.

As shown, the body measurement garment 104 may be worn by a human user 106, and is configured to produce a plurality of output signals (e.g., electrical signals) that collectively comprise output data that correspond to or may be correlated with one or more body measurements of the human user 106. The term "body measurement" refers to a measurement of length (e.g., a circumference or lateral distance) of or around a portion of the body of the human user 106 (e.g., chest, waist, arms, torso, or neck). For example, a portion of the output data produced by the body measurement garment 104 may correspond to a measurement of the waist size of the human user 106. In another example a portion of the output data produced by the body measurement garment 104 may correspond to a measurement of the neck size of the human user 106. In yet another example, a portion of the output data produced by the body measurement garment 104 may correspond to a measurement of the arm length of the human user 106.

Although the body measurement garment 104 is illustrated to resemble a shirt covering only a portion of the upper body of the human user 106, the body measurement garment 104 is not limited to such configuration, and may, in other embodiments, resemble other clothing items that cover additional or alternative portions of the body of the human user 106. For example, in other embodiments, the body measurement garment 104 may resemble a pair of pants that, when worn by the human user 106, cover the lower body of the human user 106. In another example, the body measurement garment 104 may resemble a full-body jumpsuit that, when worn by the human user 106, covers the entire body of the human user 106.

The body measurement garment 104 comprises a plurality of sensors that may, in some embodiments, be coupled to or otherwise affixed to a series of interwoven threads or fibers that provide structure to the body measurement garment 104. In other embodiments, the plurality of sensors may be coupled to tensioning belts that are affixed to the body measurement garment 104. Each of the plurality of sensors may be configured to transmit a measurable output signal to collectively form the output data produced by the body measurement garment 104. As illustrated in FIG. 1, the output data is transmitted to the computing device 108 that is responsible for generating the body shape model 102.

Upon receiving the output data from the body measurement garment 104, the computing device 108 determines one or more body measurements corresponding to the output data. The computing device 108 then uses the one or more body measurements to compose a measurement profile for the human user 106. The measurement profile is a structured data set representing a plurality of body measurements of the human user 106. Consistent with some embodiments, the computing device 108 may store the measurement profile as a data record in a local or networked database along with an identifier of the human user 106. The identifier may be used to associate the measurement profile of the human user 106 with an online user account of the human user 106. In some embodiments, the measurement profile data record may include fit preferences of the human user 106.

The computing device 108 uses the measurement profile to generate the body shape model 102. The body shape model 102 is a structured data set that provides a representation of the body of the human user 106. The body shape model 102 may be rendered (e.g., by the computer device 108) to present a three-dimensional, correctly-scaled, virtual model of the body of the human user 106.

Figure 2:
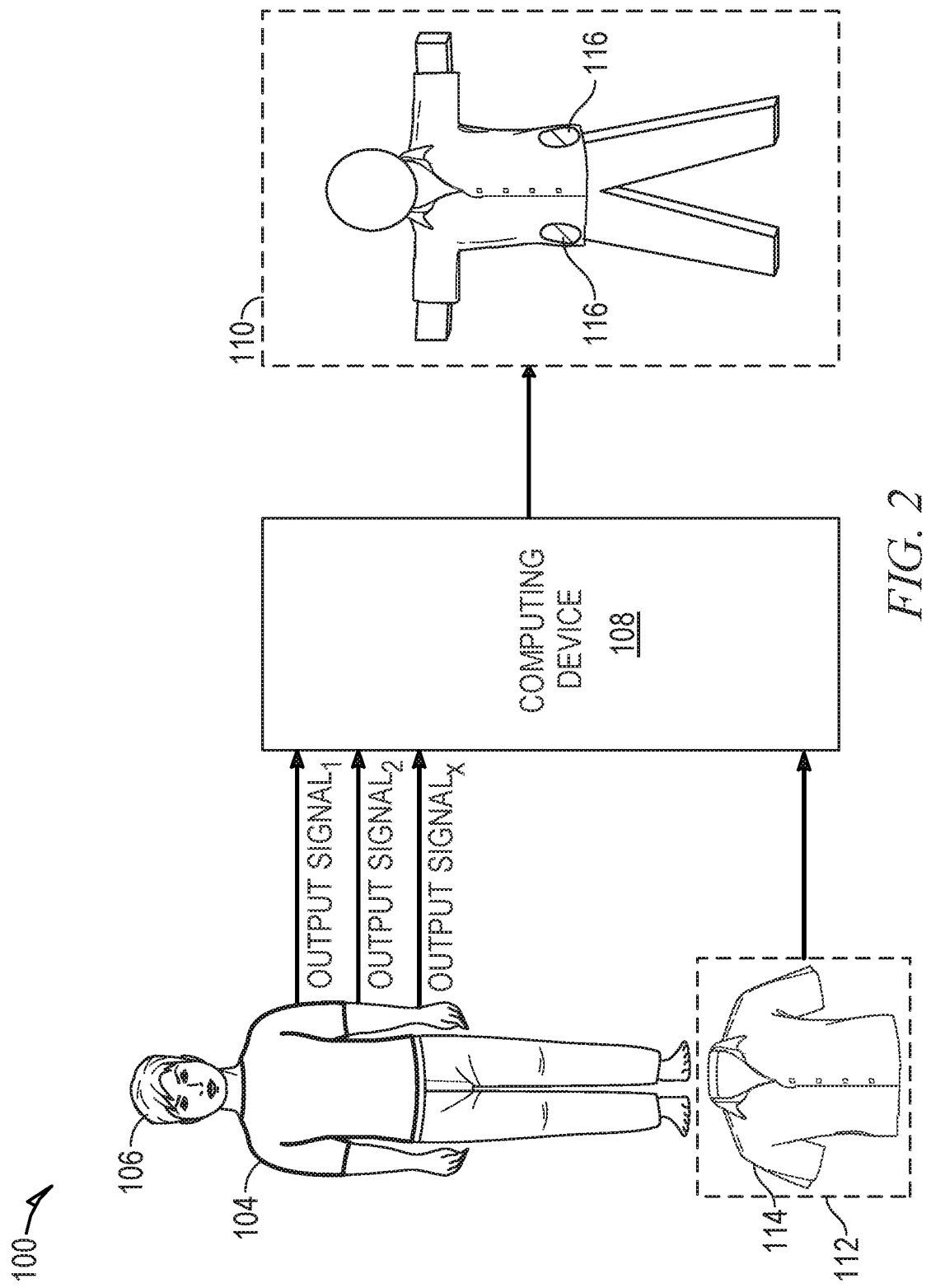
FIG. 2 is a context diagram illustrating a body measurement system configured to generate a garment fit model using a garment model, according an example embodiment.

The body shape model 102 produced by the computer device 108 may be utilized for a number of garment shopping and tailoring functions. For example, as illustrated in FIG. 2, the human user 106 may utilize the body shape model 102 (e.g., during an online commerce session) to understand how certain garments fit the human user 106. In particular, FIG. 2 is a context diagram illustrating the body measurement system 100 configured to generate a garment fit model 110 using a garment model 112, according an example embodiment. As shown in FIG. 2, the computing device 108 receives the output data produced by the body measurement garment 104 as inputs along with the garment model 112, which is a structured data set representing attributes of a physical real-world garment 114 such as dimensions. The physical real-world garment 114 may, for example, be a garment that the human user 106 is interested in purchasing. The garment model 112 may include additional information about the garment 114 including the tensile strength, elasticity, and weight of the fabric comprising the garment 114. Consistent with some embodiments, the garment model 112 may be obtained from a network-based marketplace or a garment manufacturer system that is in communication with the computing device 108 (e.g., via the Internet).

As with the process described in FIG. 1, the computing device 108 uses the output data received from the body measurement garment 104 to determine one or more body measurements of the human user 106 and compose the measurement profile of the human user 106. The computing device 108 uses the measurement profile to generate the body shape model 102 (not shown in FIG. 2). The computing device 108 may then compare the body shape model 102 with the garment model 112 to generate the garment fit model 110, which is a structured data set representing the fit of the garment 114 on the human user 106. In particular, in comparing the body shape model 102 with the garment model 112, the computer device 108 may determine the tightness (e.g., an amount of pressure exerted by the garment 114 on the human user 106) of various regions of the garment 114 on various portions of the body of the human user 106. Accordingly, the garment fit model 110 provides an indication of the tightness of the garment 114 on the human user 106. It shall be appreciated that in some embodiments, the garment fit model 110 may be generated by the computer device 108 using only the measurement profile of the human user 106 and the garment model 112 without the need for generating the body shape model 102.

The garment fit model 110 may further include an indication of portions of the garment 114 determined by the computing device 108 to exceed a predefined threshold for tightness (e.g., an amount of pressure exerted by the garment 114 on the human user 106 that is above a predefine threshold). From the perspective of the human user 106, these portions of the garment 114 may cause an uncomfortable sensation (e.g., too tight) or would provide an obstacle to the human user 106 being able to wear the garment 114. The garment fit model 110 may similarly include an indication of portions of the garment 114 determined by the computer device 108 to fall below a predefined threshold for looseness (e.g., an amount of exerted pressure that is below a predefine threshold). In some embodiments, the garment fit model 110 may also include an indication of portions of the garment 114 that may create an uncomfortable sensation (e.g., increased body heat) due to the fit, color, or fabric type of the garment 114.

The garment fit model 110 may be rendered (e.g., by the computing device 108) to present a three-dimensional virtual representation of the garment 114 being worn by the human user 106. Upon rendering the garment fit model 110, the regions of the garment 114 that are determined to exceed the predefined tightness threshold or fall below the predefined looseness threshold may be visually distinguished from the remainder of the virtual representation of the garment 114, an example of which is illustrated by regions 116 of FIG. 2.

In addition to the application of the body shape model 102 in developing the garment fit model 110, the body shape model 102 may also be utilized in the generation of personalized fitting mannequins. A personalized fitting mannequin is a physical, real-world, metrologically correct representation of a human user 106 having a plurality of embedded sensors. The personalized fitting mannequin may be employed by, for example, the human user 106 in instances in which the human user 106 wishes to shop for physical real-world garments (e.g., the garment 114) at brick-and-mortar retail location without being physically present at the brick-and-mortar retail location (e.g., by making use of a telepresence robot). In these instances, a sales associate working at the brick-and-mortar retail location may place a garment on the personalized fitting mannequin, and the human user 106 may be able to see how the garment actually fit on his body (e.g., through the video feed provided by the telepresence robot).

Additionally, the personalized fitting mannequin may be in communication with a computing device 108 of the human user 106 to provide information about how tightly or loosely fitting the garment 114 is based on the output from the plurality of sensors embedded in the personalized fitting mannequin. In this way, the personalized fitting mannequin provides an alternative embodiment for generating a garment fit model 110. As an example of this process, FIG. 3 is a context diagram illustrating the body measurement system 100 configured to generate the garment fit model 110 using output from a personalized fitting mannequin 120, according to an example embodiment.

Figure 3:
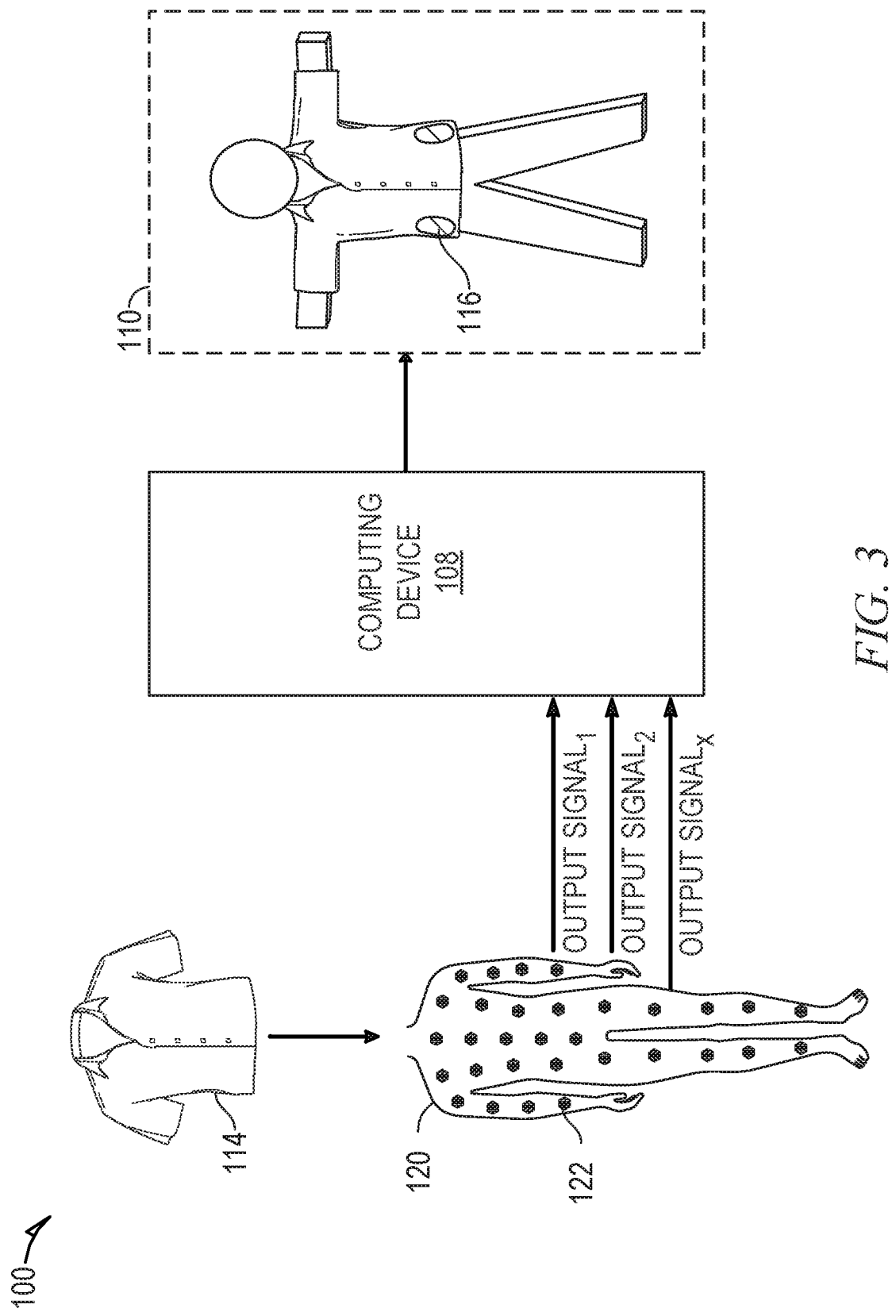
FIG. 3 is a context diagram illustrating a body measurement system configured to generate a garment fit model using output from a personalized fitting mannequin, according to an example embodiment.

As shown in FIG. 3, the personalized fitting mannequin 120 includes a number of strategically placed sensors 122, each of which produce an output signal that corresponds to or may be correlated with the tightness of the garment 114 when placed on the personalized fitting mannequin 120. Because the personalized fitting mannequin 120 is a metrologically correct representation of the human user 106, the output data produced by the personalized fitting mannequin 120 corresponds to the actual tightness of the garment 114 on the human user 106 (not shown in FIG. 3). In an example, at least a portion of the sensors 122 may be pressure sensors configured to measure the pressure (e.g., as a unit of force per area) exerted by the garment 114 on a portion of the personalized fitting mannequin 120. In some embodiments, at least a portion of the sensors 122 may be operable to measure a sensation (e.g., itchiness) of the fabric of garment 114 on the skin of the human user 106.

The personalized fitting mannequin 120 is communicatively coupled to the computing device 108 (e.g., over a network) to enable the transmission of the output data produced by the personalized fitting mannequin 120 to the computing device 108. Upon receiving the output data from the personalized fitting mannequin 120, the computing device 108 processes the signals to generate the garment fit model 110, which is described above in reference to FIG. 2.

Figure 4A:
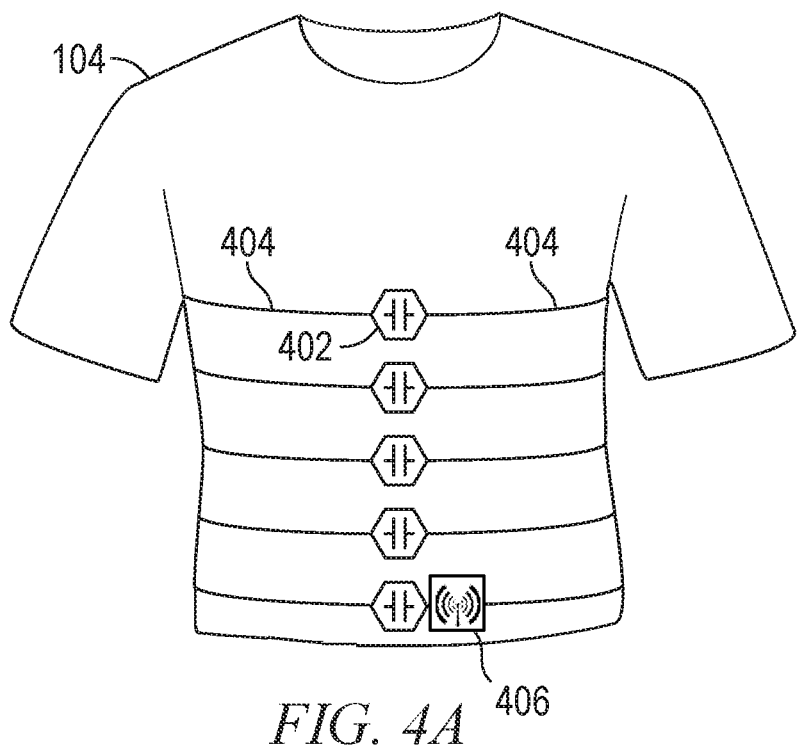
FIG. 4A is a block diagram illustrating a body measurement garment, according to an example embodiment.

FIG. 4A is a block diagram illustrating the body measurement garment 104, according to an example embodiment. As shown, the body measurement garment 104 comprises a number of embedded sensors 402, each of which are configured to produce a measurable output. A variety of different types of sensors 402 may be employed, and the output of each sensor 402 may depend on the type of sensor 402 employed. The sensors 402 may, for example, include tension sensors, resistance sensors, compression sensors, acceleration sensors, friction sensors, rotational sensors, humidity sensors, or other force sensors.

In some embodiments, at least one of the plurality of sensors 402 is configured to receive manual adjustments from the human user 106 (e.g., a haptic sensor). The manual adjustments received from the human user 106 may be used to adjust or modify the eventually generated measurement profile or body shape model 102 in accordance with the desires of the user 106. For example, the human user 106 may prefer clothing that is loose around the waist. Following this example, the human user 106 may provide input to one or more sensors to change the output data in such a manner that when the output data is correlated to a plurality of body measurements, the measurement of the waist of the human user 106 is increased.

As shown in FIG. 4A, each of the sensors 402 may be coupled to a tensioning band 404 that is positioned on the body measurement garment 104 such that each tensioning band 404 spans an area of the body of the human user 106 that is to be measured. The tensioning bands 404 may, for example, be a strap, a rope, a cord, a thread, a string, or a belt made from any non-rigid material or fiber of a known length. In some embodiments, the tensioning bands 404 may collectively comprise the structure of the body measurement garment 104, while in other embodiments, the tensioning bands 404 are affixed to a series of threads or fibers forming the structure of the body measurement garment 104.

In an example, a tensioning band 404 may form a measurable circumference (e.g., in a unit of length) around an axis of the body of the human user 106 such as the arm, leg, chest, neck, or waist. Following this example, the sensors 402 may comprise a spring-loaded spool that is coupled to the tensioning band 404, and allows the sensor 402 to measure the tension (e.g., as a unit of force) exerted by the portion of the body of the human user 106 on the tensioning band 404. The measured tension is provided as output data by the sensor 402 to the computing device 108. Given a known length of the tensioning band 404, the computing device 108 may then correlate the output data from the sensor 402 with a length measurement (e.g., a circumference or lateral distance).

The sensors 402 are further coupled to one or more transmitters 406 capable of transmitting the output data from each of the sensors 402 to the computing device 108. The one or more transmitters 406 may be capable of transmitting the output data from the sensors 402 through either wired or wireless mediums. In some embodiments, multiple sensors 402 may be coupled to a single transmitter 406 capable of transmitting the output data from the multiple sensors 402 as a single data packet.

In some embodiments, each of the sensors 402 is coupled to or includes a respective wireless transmitter 406 for transmitting output data. The transmitters 406 may transmit the output data from the sensors 402 using a low energy transmission protocol such as Bluetooth low energy (BLE). The utilization of these low energy wireless transmitters 406 may achieve a technical effect of reducing the power consumed by the body measurement garment 104 while increasing the granularity and accuracy of the eventually produced body measurements.

It shall be appreciated that although the body measurement garment 104 is illustrated in FIG. 4A to include a certain number of sensors 402 and tension bands 404, in other embodiments, the body measurement garment 104 may include fewer or additional sensors 402 or tension bands 404. Further, it shall be appreciated that although FIG. 4A illustrates the sensors 402 and tension bands 404 in a particular position on the body measurement garment 104, the body measurement garment 104 is not limited to such a configuration, and a variety of other configurations may be employed. For example, in some embodiments, the body measurement garment 104 may include one or more tension bands 404 that are positioned laterally along the extremities or torso of the human user 106. In this manner, the tension bands 404 enable the sensors 402 to provide measurements of the lateral distance of portions of the body of the human user 106 such as an arm length, leg length, and torso length.

Figure 4B:
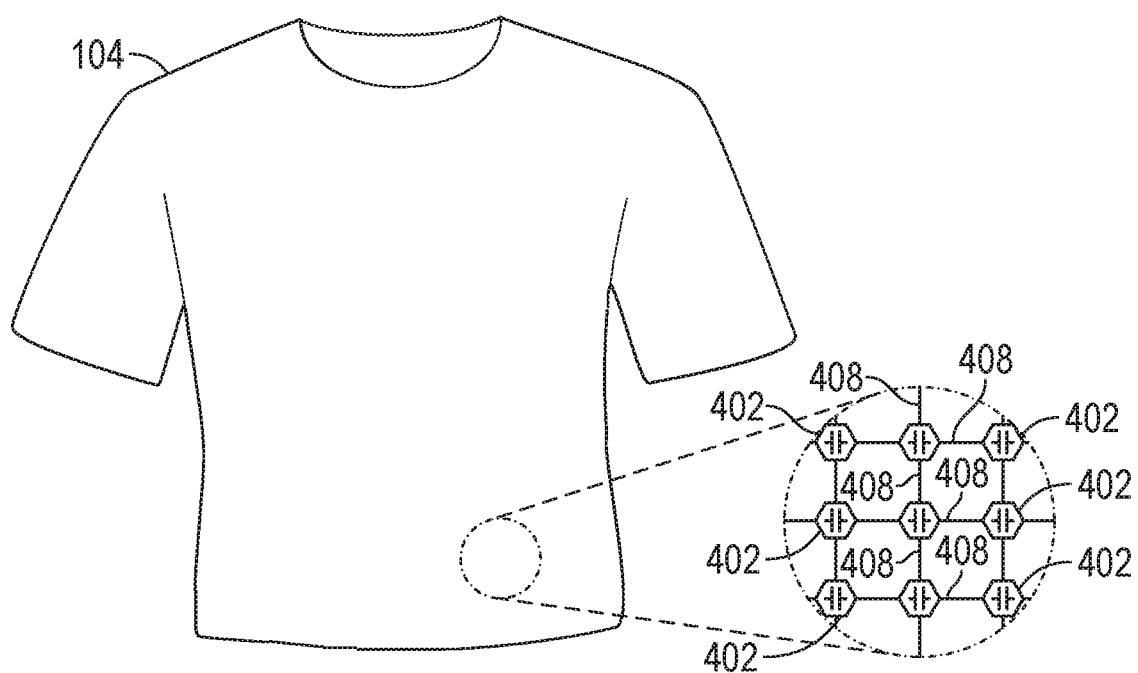
FIG. 4B is a block diagram illustrating a body measurement garment, according to an alternative embodiment

As another example, FIG. 4B is a block diagram illustrating the body measurement garment 104, according to an alternative embodiment. As shown, the body measurement garment 104 includes a plurality of sensors 402 coupled to intersections of interwoven threads 408 forming the structure of the body measurement garment 104. Each of the sensors 402 may be coupled to the threads 408 by one or more spring loaded spools allowing the sensors 402 to measure the tension exerted by the human user 106 on portions of the body measurement garment 104. In this way, the plurality of sensors 402 produce a mesh network of sensory output that is transmitted (e.g., by way of a transmitter such as the transmitters 406 described in reference to FIG. 4A) to the computer device 108. The computer device 108 may, in turn, perform a finite element analysis on the mesh network of sensory output whereby the computer device 108 algorithmically groups sections of the mesh network of sensory output into uniform blocks, and determines a force measurement corresponding to each uniform block. The computer device 108 further determines a tension measurement corresponding to each uniform block based on the respective force measurement and area of the uniform block.

Figure 5:
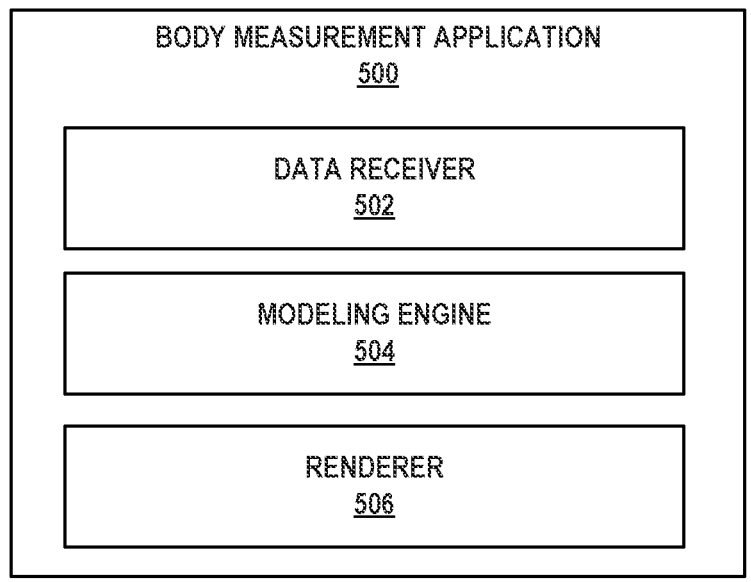
FIG. 5 is a block diagram illustrating various functional components of a body measurement application, according to an example embodiment.

FIG. 5 is a block diagram illustrating various functional components of a body measurement application 500, according to an example embodiment. The body measurement application 500 may be executed by the computing device 108 to perform the functions described below. As is understood by skilled artisans in the relevant computer and Internet-related arts, each component (e.g., a module or engine) illustrated in FIG. 5 may represent a set of logic (e.g., executable software instructions) and the corresponding hardware (e.g., memory and processor) for executing the set of logic.

The body measurement application 500 is illustrated in FIG. 5 as including a data receiver 502, a modeling engine 504, and a renderer 506, all configured to communicate with each other (e.g., via a bus, shared memory, a switch, or application programming interfaces (APIs)). The various components of the body measurement application 500 may be in communication with the body measurement garment 104. Furthermore, each of the various components of the body measurement application 500 may access one or more network databases, and each of the various components of the body measurement application 500 may be in communication with one or more of the third party applications. Further, while the components depicted in FIG. 5 are discussed in the singular sense, it will be appreciated that in other embodiments multiple instances of any one of these components may be employed.

The data receiver 502 is configured to receive output data from the body measurement garment 104. The data receiver 502 may be configured to receive data transmitted using a low energy transmission protocol (e.g., BLE), consistent with some embodiments. The data receiver 502 is further configured to provide the output data, received from the body measurement garment 104, to the modeling engine 504.

The modeling engine 504 is configured to generate a number of data profiles and models using the output data of the body measurement garment 104. For example, the modeling engine 504 may use the output data to compose a measurement profile for the user 106 associated the output data (e.g., the user 106 wearing the body measurement garment 104 at the time the output data is received). The measurement profile is a structured data set comprising a plurality of body measurements of the user 106. The modeling engine 504 may compose the measurement profile by calculating one or more length measurements using the output data. For example, in instances in which the output data corresponds to a measure of tension exerted by the body of the user 106 on the body measurement garment 104, the modeling engine 504 may use the tension measurement in combination with a known length associated with the corresponding portion of the body measurement garment 104 to generate the length measurement.

The modeling engine 504 uses the measurement profile to generate a corresponding body shape model 102 for the user 106. The body shape model 102 is a structured data set that represents the shape of body of the user 106 with accurate dimension measurements, and may be rendered by the renderer 506 to present a three-dimensional model of the user 106 (e.g., on the computing device 108).

The modeling engine 504 may further generate a garment fit model 110 representing the fit of a particular garment 114 on a particular user 106. The modeling engine 504 may generate the garment fit model 110 by comparing the measurement profile (or body shape model 102) with the garment model 112, which is a structured data set representing the dimensions of the particular garment 114. In generating the garment fit model 110, the modeling engine 504 may determine the tightness of regions of the garment 114 on portions of the body of the user 106 (e.g., an amount or pressure exerted by the garment 114 on the user 106). The modeling engine 504 may further identify regions of the garment 114 that are either above a predefined tightness threshold or below a predefined looseness threshold. The render 506 may render the garment fit model 110 to present (e.g., on the computer device 108) a three-dimensional, correctly scaled, virtual representation of the user 106 wearing the garment 114. In rendering the garment fit model 110, the renderer 506 may cause the regions (e.g., regions 116) of the garment 114 that were determined to be either too tight (e.g., above the threshold level of tightness) or too loose (e.g., below the looseness threshold) to be visually distinguished from the remainder of the virtual representation of the garment 114. For example, the renderer 506 may use the color red to distinguish regions that are too tight, and the color yellow to distinguish regions of the garment that are too loose.

The modeling engine 504 may further utilize the output from the body measurement garment 104 to develop a garment wear model for the user 106. The garment wear model is a structured data set representing the wear pattern of the user 106. The modeling engine 504 may generate the wear model for the user 106 by analyzing multiple sets of output data produced by the body measurement garment 104 with at least a portion of the sets of output data being produced while the user 106 is wearing the body measurement garment 104 while in motion. The modeling engine 504 analyzes the multiple sets of data to determine a normal wear pattern of the user 106. The "normal wear pattern" refers to how the user 106 may, over time, damage, erode, or destroy portions of the garment 114 by friction or over use. For example, the manner in which the user 106 walks may cause added friction to the inner thigh region of trousers, which over time results in a wear pattern that damages the crotch region of the trousers. The modeling engine 504 may further generate garment specific garment wear models by comparing the multiple sets of output data with the garment model 112. The renderer 506 renders the garment wear model to present a three-dimensional virtual representation of the user 106 wearing the garment 114 (either a generic garment or a specific garment) with visual indications (e.g., hatching or highlighting) of the normal wear pattern.

Figure 6:
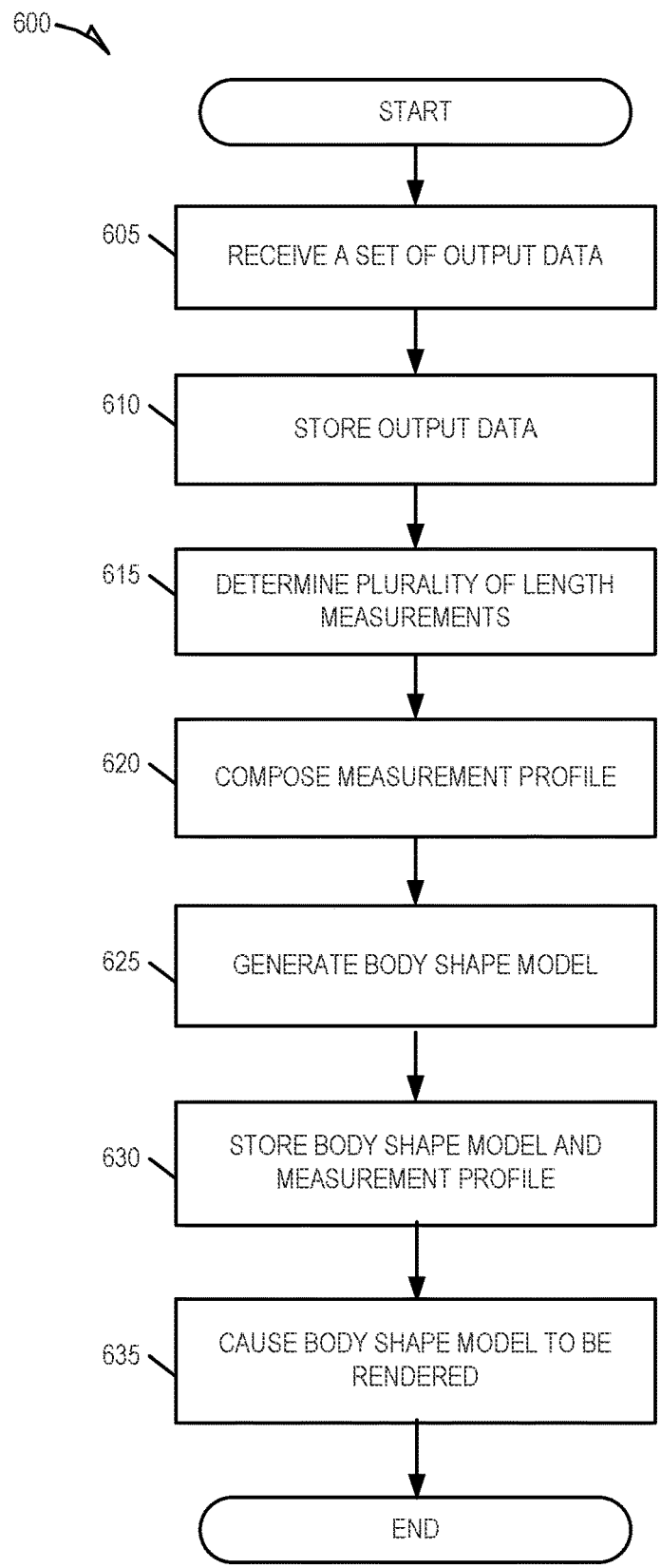
FIG. 6 is a flowchart illustrating a method for generating a body shape model, according to an example embodiment.

FIG. 6 is a flowchart illustrating a method 600 for generating a body shape model, according to an example embodiment. The method 600 may be embodied in computer-readable instructions for execution by one or more processors such that the steps of the method 600 may be performed in part or in whole by the computing device 108. In particular, the method 600 may be carried out by the functional components of the body measurement application 500, and accordingly, the method 600 is described below, by way of example with reference thereto. However, it shall be appreciated that the method 600 may be deployed on various other hardware configurations and is not intended to be limited to the computing device 108 or the functional components of the body measurement application 500.

At operation 605, the data receiver 502 receives a set of output data from the body measurement garment 104 worn by the human user 106. The set of output data is produced by the plurality of sensors 402 embedded in the body measurement garment 104. At operation 610, the data receiver 502 stores the set of output data. The output data may, for example, be stored in a machine-readable medium of the computing device 108 or in a networked database communicatively coupled to the computing device 108.

At operation 615, the modeling engine 504 processes the set of output data to determine a plurality of length measurements corresponding to body measurements of the human user 106. In an example, the set of output data corresponds to a measure of force (e.g., tension) applied to tensioning bands 404 coupled to the plurality of sensors 402, and the modeling engine 504 uses the force measurements in combination with known lengths of the tensioning bands 404 to calculate the length measurements. In another example, the sensors 402 may comprise a spring loaded spool coupled to the tension bands 404, and the sensors 402 may be configured to measure various lengths of individual tension bands 404 displaced by the human user 106 wearing the body measurement garment 104. In some embodiments, the set of output may include one or more output signals from one or more sensors 402 configured to receive manual adjustments from the human user 106. In this manner, the human user 106 may cause the length measurement of a particular region of his body to be increased or decreased thereby modifying the eventually generated body shape model 102 of the human user 106.

At operation 620, the modeling engine 504 uses the plurality of length measurements to compose a measurement profile for the human user 106. At operation 625, the modeling engine 504 uses the measurement profile of the human user 106 to generate a body shape model 102 for the human user 106. In instances in which the output data includes manual adjustments from the human user 106, the modeling engine 504 generates the body shape model 102 in accordance with the manual adjustments.

At operation 630, the modeling engine 504 causes the measurement profile and the body shape model 102 to be stored in a repository (e.g., a database) of user profiles in a manner such that the measurement profile and the body shape model 102 are associated with an electronic user profile (e.g., maintained by a network-based marketplace) of the human user 106. At operation 635, the renderer 506 causes the body shape model 102 to be rendered. For example, the renderer 506 may provide a set of instructions to the computing device 108 that cause the computing device 108 to render the body shape model 102. Upon rendering the body shape model 102, a three-dimensional virtual representation of the human user 106 with accurately scaled body measurements is presented (e.g., on computing device 108).

Figure 7:
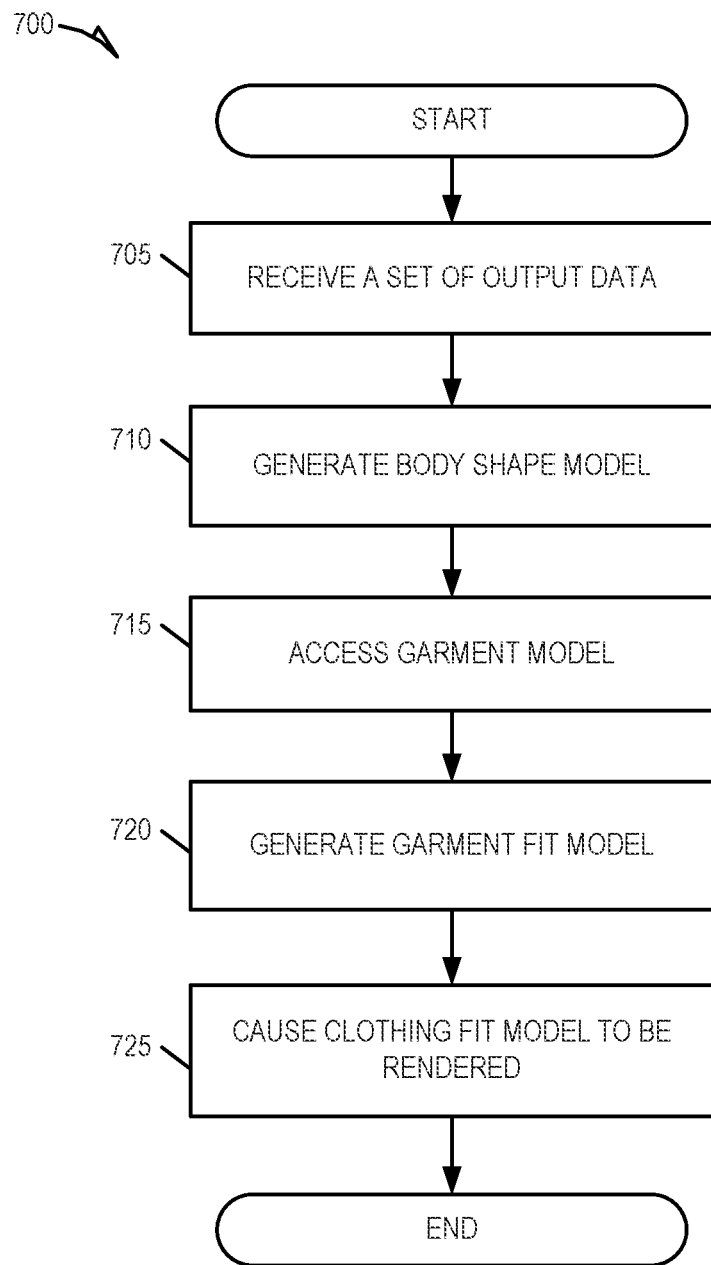
FIG. 7 is a flowchart illustrating a method for generating a garment fit model, according to an example embodiment.

FIG. 7 is a flowchart illustrating a method 700 for generating a garment fit model 110, according to an example embodiment. The method 700 may be embodied in computer-readable instructions for execution by one or more processors such that the steps of the method 700 may be performed in part or in whole by the computing device 108. In particular, the method 700 may be carried out by the functional components of the body measurement application 500, and accordingly, the method 700 is described below, by way of example with reference thereto. However, it shall be appreciated that the method 700 may be deployed on various other hardware configurations and is not intended to be limited to the computing device 108 or the functional components of the body measurement application 500.

At operation 705, the data receiver 502 receives a set of output data from the body measurement garment 104 worn by the human user 106. At operation 710, the modeling engine 704 generates a body shape model 102 corresponding to the human user 106. At operation 715, the modeling engine 504 accesses a garment model 112 defining the dimensions of a physical real-world garment 114. The garment model 112 may be obtained from a network-based marketplace or a manufacturer of the garment 114. The particular garment model 112 accessed by the modeling engine 504 may be based on a selection made by the human user 106 on a shopping interface during an online shopping session hosted by a network-based marketplace.

At operation 720, the modeling engine 504 generates a garment fit model 110 that represents the fit of the garment 114 on the human user 106. The modeling engine 504 may generate the garment fit model 110 by comparing the body shape model 102 with the garment model 112. Further details of the operation 720, according to an example embodiment, are described below in reference to FIG. 8.

At operation 725, the renderer 506 causes the body shape model 102 to be rendered. For example, the renderer 506 may provide a set of instructions to the computing device 108 that cause the computing device 108 to render the garment fit model. Upon rendering garment fit model, a three-dimensional virtual representation of the human user 106 wearing the garment 114 is presented (e.g., on computing device 108). The presentation of the human user 106 wearing the garment 114 may include visual indications (e.g., hatching, bolding, or highlighting) of areas identified by the modeling engine 504 to be too tight or too loose.

Figure 8:
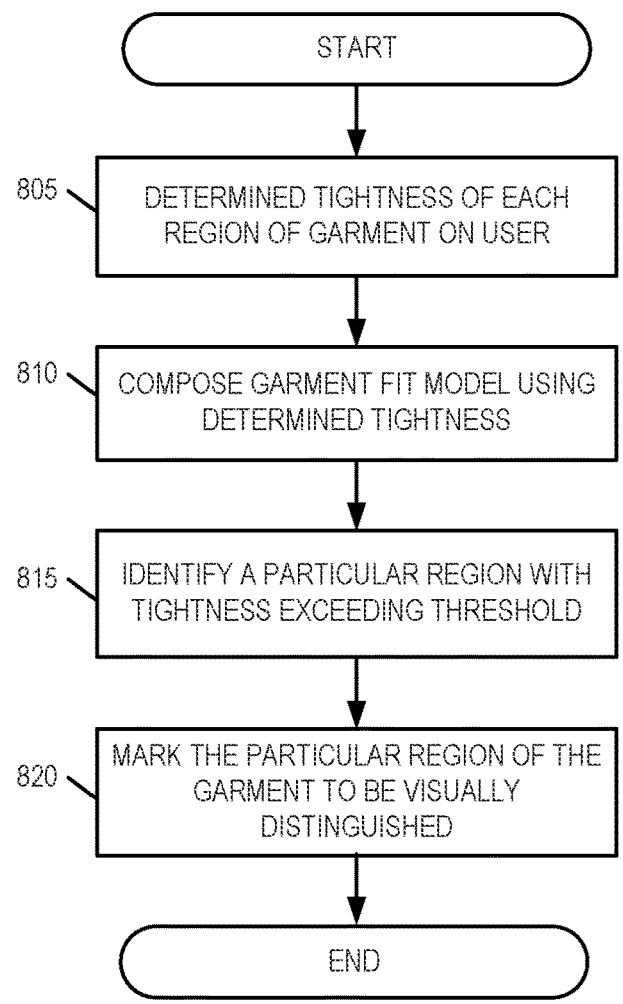
FIG. 8 is a flowchart illustrating a method for determining pressure points of a real-world garment on a user, according to an example embodiment.

FIG. 8 is a flowchart illustrating a method 800 for determining regions of excess tightness of a real-world garment 114 on a user 106, according to an example embodiment. The method 800 may be embodied in computer-readable instructions for execution by one or more processors such that the steps of the method 800 may be performed in part or in whole by the computing device 108. In particular, the method 800 may be carried out by the functional components of the body measurement application 500, and accordingly, the method 800 is described below by way of example with reference thereto. However, it shall be appreciated that the method 800 may be deployed on various other hardware configurations and is not intended to be limited to the computing device 108 or the functional components of the body measurement application 500.

At operation 805, the modeling engine 504 determines the tightness of each region of the garment 114 on the human user 106. For example, the modeling engine 504 may analyze and compare information about the garment 114 (e.g., dimensions and tensile strength) stored in the garment model 112 with the body shape model 102 to calculate an amount of pressure (e.g., force applied over an area) exerted by each region of the garment 114 on various corresponding portions of the human user 106. The determined tightness of each region may then be used by the modeling engine 504 to compose the garment fit model, at operation 810.

At operation 815, the modeling engine 504 identifies a particular region of the garment 114 with a tightness exceeding a predefined tightness threshold. For example, the modeling engine 520 may determine that the pressure exerted by the sleeves of the garment on the shoulders of the human user 106 exceeds a predefined threshold. In operation 820, the modeling engine 504 marks the particular region of the garment 114 to be visually distinguished from the remainder of the visual representation of the garment 114 upon rendering the garment fit model. For example, the modeling engine 504 may instantiate a flag or other indicator associated with the region of the garment 114 in the structured data set comprising the garment model 112.

Figure 9:
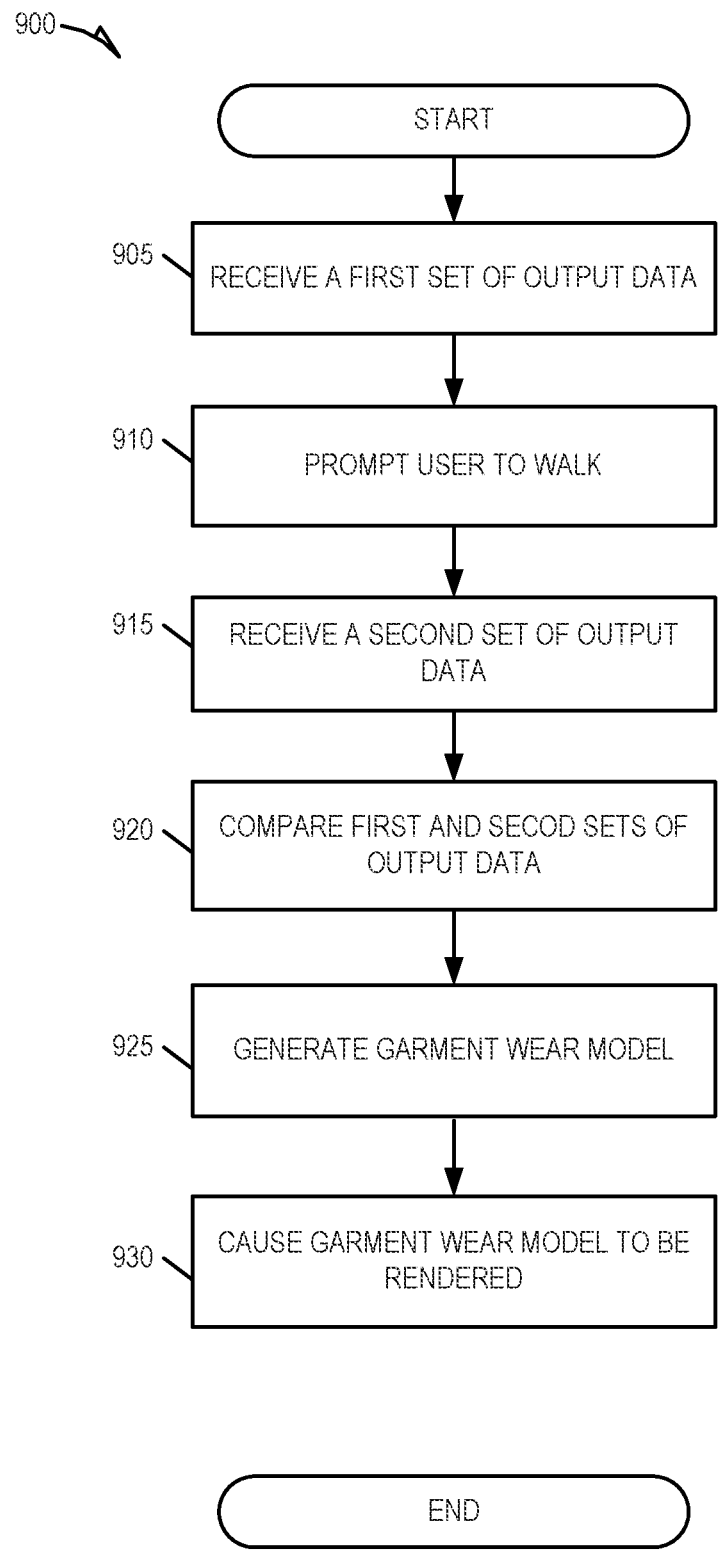
FIG. 9 is a flowchart illustrating a method for generating a garment wear model, according to an example embodiment.

FIG. 9 is a flowchart illustrating a method 900 for generating a garment wear model, according to an example embodiment. The method 900 may be embodied in computer-readable instructions for execution by one or more processors such that the steps of the method 900 may be performed in part or in whole by the computing device 108. In particular, the method 900 may be carried out by the functional components of the body measurement application 500, and accordingly, the method 900 is described below by way of example with reference thereto. However, it shall be appreciated that the method 900 may be deployed on various other hardware configurations and is not intended to be limited to the computing device 108 or the functional components of the body measurement application 500.

At operation 905, the data receiver 502 receives a first set of output data from the body measurement garment 104 worn by the human user 106. The first set of output data is received while the human user 106 is stationary. At operation 910, the computing device 108 prompts the human user 106 to walk while wear the body measurement garment 104. For example, the computing device 108 may, for example, display a user interface that instructs the human user 106 to walk. In another example, the computing device 108 may provide computer-readable instructions to a client device of the user 106 that cause the client device to display a user interface that instructs the human user 106 to walk.

At operation 915, the data receiver 502 receives a second set of output data from the body measurement garment 104 while the human user 106 is in motion. At operation 920, the modeling engine 504 compares the first set of output data with the second set of output data to determine how the movement of the human user 106 changes the output data received from the body measurement garment 104. In particular, for each set of output data, the modeling engine 504 calculates an amount of pressure exerted by portions of the body of the human user 106 on the various regions 116 of the body measurement garment 104. The modeling engine 504 then compares the pressure measurements corresponding to the first set of output data with the pressure measurements corresponding to the second set of output data. In this way, the first set of output data may serve as a baseline for comparison with subsequent sets of output data to understand how the movement of the human user 106 affects the pressure exerted on a garment 114 worn by the human user 106.

At operation 925, the modeling engine 504 generates a garment wear model based on the comparison of the first and second set of output data. The garment wear model defines a normal wear pattern of the human user 106. As such, the generating of the garment wear model may include identifying regions of a garment 114 where excessive wear that may lead to damage may occur. In some embodiments, the generation of garment wear model by the modeling engine 504 may be further based on output from one or more friction sensors included in the second set of output data. In some embodiments, the garment wear model may be garment specific, and as such, the generation of garment wear model by the modeling engine 504 may include accessing a garment model 112 and incorporating information from the garment model 112 in the garment wear model.

At operation 930, the renderer 506 causes the garment wear model to be rendered. For example, the renderer 506 may provide a set of instructions to the computing device 108 that cause the computing device 108 to render the garment wear model. Upon rendering the garment wear model, a three-dimensional virtual representation of the human user 106 wearing a garment (either general or specific) is presented (e.g., on computing device 108). The presentation of the garment wear model may include visual indications (e.g., hatching, bolding, or highlighting) of the normal wear pattern of the user 106, and additional indications of areas in which excessive wear may occur.

Figure 10:
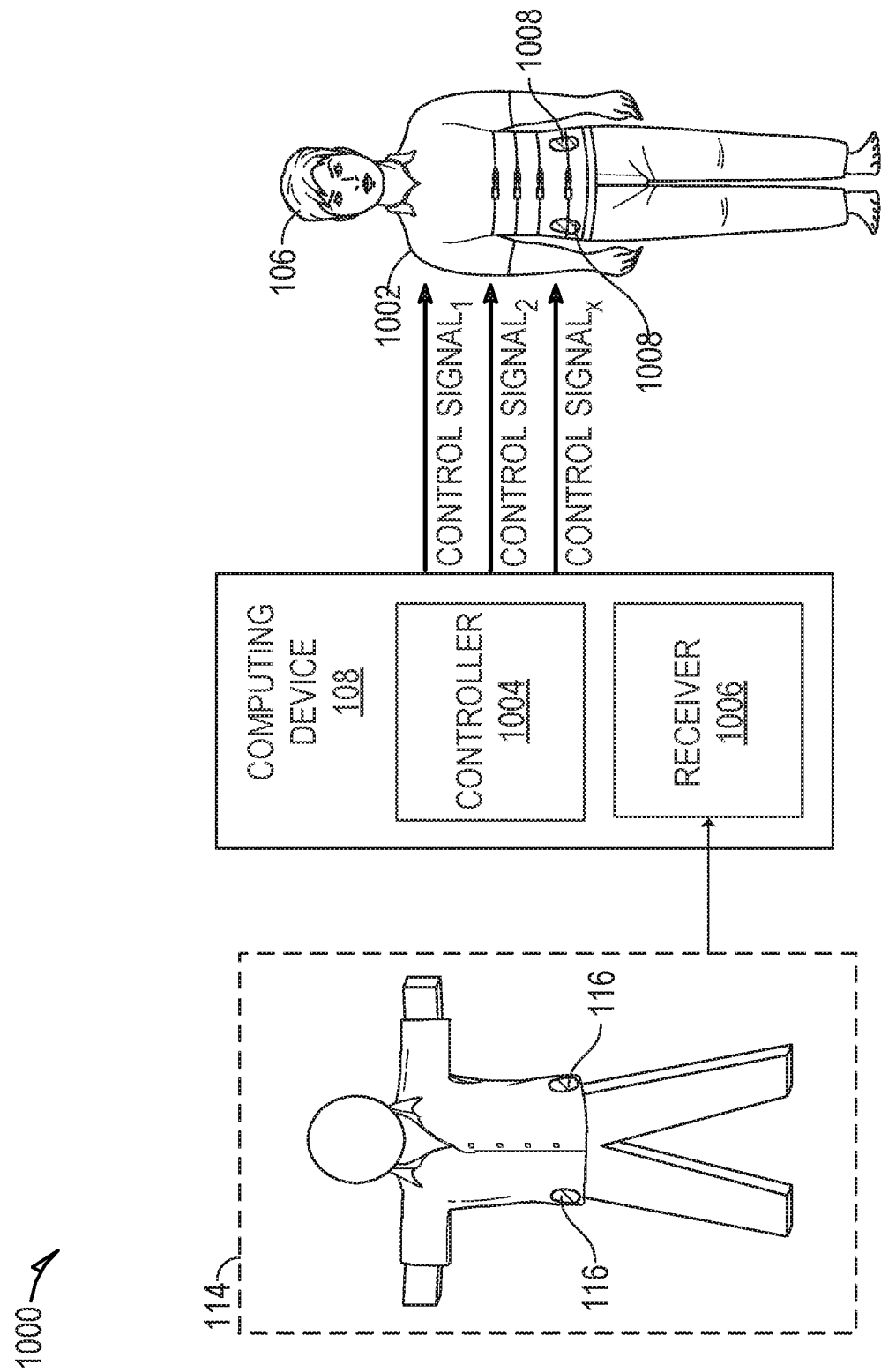
FIG. 10 is a context diagram illustrating a fit simulation system configured to simulate a garment fit on a human user, according to an example embodiment.

FIG. 10 is a context diagram illustrating a fit simulation system 1000 configured to simulate a garment fit on the human user 106, according to an example embodiment. To avoid obscuring the inventive subject matter with unnecessary detail, various functional components (e.g., modules and engines) that are not germane to conveying an understanding of the inventive subject matter have been omitted from FIG. 10. However, a skilled artisan will readily recognize that various additional functional components may be supported by the fit simulation system 1000 to facilitate additional functionality that is not specifically described herein.

As shown, a fit simulation garment 1002 is able to be worn by a human user 106, and is configured to receive a plurality of control signals (e.g., electrical signals) that collectively comprise control data. The control data causes the fit simulation garment 1002 to simulate the fit of the garment 114 on the user 106. In this particular example, the control data causes the fit simulation garment 1002 to simulate the fit of the garment 114 on the human user 106.

Although the fit simulation garment 1002 is illustrated to resemble a shirt covering only a portion of the upper body of the human user 106, the fit simulation garment 1002 is not limited to such a configuration, and may, in other embodiments, resemble other clothing items that cover additional or alternative portions of the body of the human user 106. For example, in other embodiments, the fit simulation garment 1002 may resemble a pair of pants that, when worn by the human user 106, cover the lower body of the human user 106. In another example, the fit simulation garment 1002 may resemble a full-body jumpsuit that, when worn by the human user 106, covers the entire body of the human user 106.

The fit simulation garment 1002 may comprise a plurality of actuators that are collectively configured to produce the simulation of a particular garment (e.g., the garment 114) being worn by the user 106. In some embodiments, the actuators may be coupled to or otherwise affixed to a series of interwoven threads or fibers that provide structure to the body measurement garment 104. Each of the plurality of actuators may be configured to receive one or more control signals from a controller 1004 that may, in some embodiments, be included in the computing device 108.

The control data provided to the fit simulation garment 1002 by the controller 1004 may depend on a garment fit model 110 received by a receiver 1006 communicatively coupled to the controller 1004 (e.g., via a bus, shared memory, a switch, or application programming interfaces (APIs)). In this example, the receiver 1006 receives the garment fit model 110 that represents the fit of the garment 114 on the human user 106. The garment fit model 110 may be accessed from a network database communicatively coupled to the computing device 108 or obtained from a network-based marketplace. Upon accessing the garment fit model 110, the receiver 1006 forwards the garment fit model 110 to the controller 1004, and the controller 1004, in turn, parses the garment fit model 110 to generate and transmit the control data (e.g., the plurality of control signals).

The control data transmitted by the controller 1004 to the fit simulation garment 1002 causes one or more actuators to simulate tightness of a region of the garment 114 on the human user 106. For example, the control signals provided by the controller 1004 may cause the fit simulation garment 1002 to increase an amount of compression applied by regions 1008 of the fit simulation garment 1002 on a corresponding portion of the body of the human user 106 by causing the actuator to apply an amount of tension on the threads comprising regions 1008, to which the actuator is coupled.

More specifically, in the example embodiment illustrated in FIG. 10, the garment fit model 110 provides an indication of the tightness of regions 116 of the garment 114 on the human user 106. Accordingly, the control data generated by the controller 1004, upon parsing the garment fit model 110, causes the regions 1008 of the fit simulation garment 1002 to simulate the corresponding tightness of the regions 116 of the actual garment 114.

Although the controller 1004 and receiver 1006 have been discussed and are illustrated as being integrated as part of the computing device 108, it shall be appreciated that, in alternative embodiments, the controller 1004 and receiver 1006 may form part of or be integrated with another computing device. Further, either one of the controller 1004 or receiver 1006 may form part of or be integrated into a hardware component that is separate and distinct from a computing device.

Figure 11:
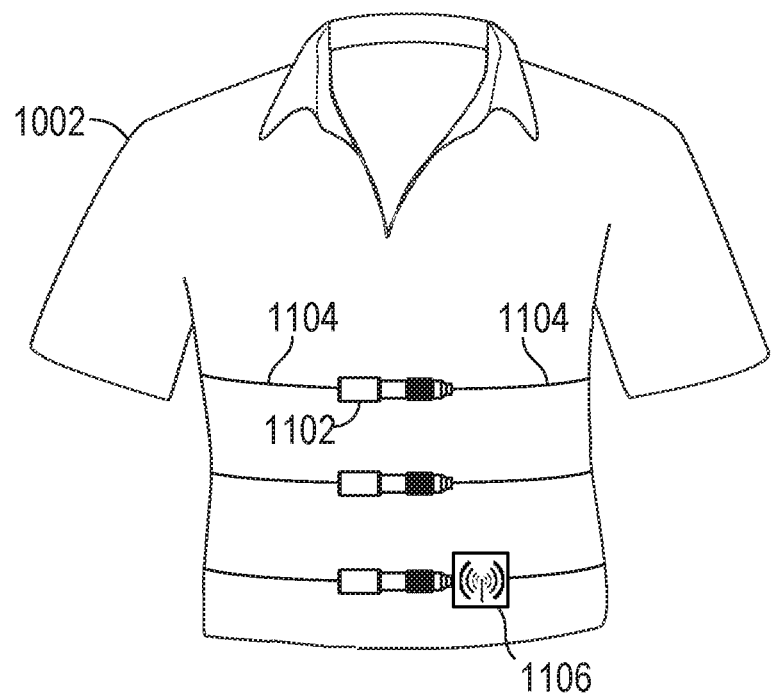
FIG. 11 is a block diagram illustrating a fit simulation garment, which is provided as part of the garment fit simulation system, according to an example embodiment.

FIG. 11 is a block diagram illustrating the fit simulation garment 1002, which is provided as part of the garment fit simulation system, according to an example embodiment. As shown, the fit simulation garment 1002 comprises multiple actuators 1102, each of which are configured to simulate tightness of various regions 1008 of fit simulation garment 1002. A variety of different types of actuators 1102 may be employed, and the manner in which each one of the actuators 1102 simulates tightness depends on the types of actuators 1102 employed.

As shown in FIG. 11, each of the actuators 1102 may be coupled to a tensioning band 1104 that is positioned on the fit simulation garment 1002 such that the tensioning band 1104 spans an area of the body of the human user 106. The tensioning bands 1104 may be, for example, a strap, a rope, a cord, a thread, or a belt made from any material or fiber of a known length. In some embodiments, the tensioning bands 1104 may collectively comprise the structure of the fit simulation garment 1002, while in other embodiments, the tensioning bands 1104 are affixed to a series of horizontally and vertically run threads or fibers forming the structure of the body measurement garment 104.

In an example, a tensioning band 1104 may form a circumference (e.g., in a unit of length) around an axis of the body of the human user 106 such as the arm, leg, chest, neck, or waist. Following this example, each of the actuators 1102 may comprise a motorized spool, and each of the tensioning bands 1104 may be wound around the spool. In this way, the actuators 1102 acts to increase or decrease the length of the tensioning bands 1104, thereby causing portions of the fit simulation garment 1002 to constrict or expand thus simulating the tightness (or looseness) of corresponding portions of the garment 114 on the human user 106.

The actuators 1102 are further coupled to one or more receivers 1006 capable of receiving command data from the controller 1004. The receivers 1006 may be capable of receiving the command data from the controller 1004 through either wired or wireless mediums. In some embodiments, multiple actuators 1102 may be coupled to a single receiver 1006 capable of provisioning the control signals comprising the control data to the appropriate actuators 1102.

In some embodiments, each of the actuators 1102 is coupled to or includes a respective wireless receiver 1006 for receiving the control data. The wireless receivers 1006 may be configured to receive control data transmitted by the controller 1004 using a low energy transmission protocol such as BLE.

It shall be appreciated that although the fit simulation garment 1002 is illustrated in FIG. 11 to include a certain number of actuators 1102 and tensioning bands 1104, in other embodiments, the fit simulation garment 1002 may include fewer or additional actuators 1102 or tensioning bands 1104. Further, it shall be appreciated that although FIG. 11 illustrates the fit simulation garment 1002 as including actuators 1102 and tensioning bands 1104 in a particular configuration and in a particular position on the fit simulation garment 1002, fit simulation garment 1002 is not limited to such a configuration, and a variety of other configurations may be employed.

For example, in some embodiments, the fit simulation garment 1002 may additionally or alternatively comprise tensioning bands 1104 that traverse the longitudinal axis of the body of the human user 106 (as opposed to the illustrated tensioning bands 1104, which traverse run perpendicular to the longitudinal axis of the body of the human user 106). Further, in some embodiments, a portion of the actuators 1102 of the fit simulation garment 1002 may comprise an inflatable air pocket coupled to a pump capable of inflating or deflating the inflatable pockets so as to simulate the tightness of regions of a garment on the human user 106. In some embodiments, the fit simulation garment 1002 may not include tensioning bands 1104, and the plurality of actuators 1102 may be instead coupled to the intersections of the threads or fibers forming the structure of the fit simulation garment 1002.

In some embodiments, the fit simulation garment 1002 may be combined with the body measurement garment 104 to form a garment having both a plurality of sensors 402 (e.g., to produce data corresponding to body measurements) and a plurality of actuators 1102 (e.g., to simulate the tightness of regions 116 of a garment 114 on a user 106). In these embodiments, the plurality of sensors 402 and the plurality of actuators 1102 may form a mesh network similar to that which is illustrated in FIG. 4B wherein the sensors 402 and the actuators 1102 are affixed or coupled to intersections of the interwoven threads or fibers forming the structure of the garment.

Figure 12:
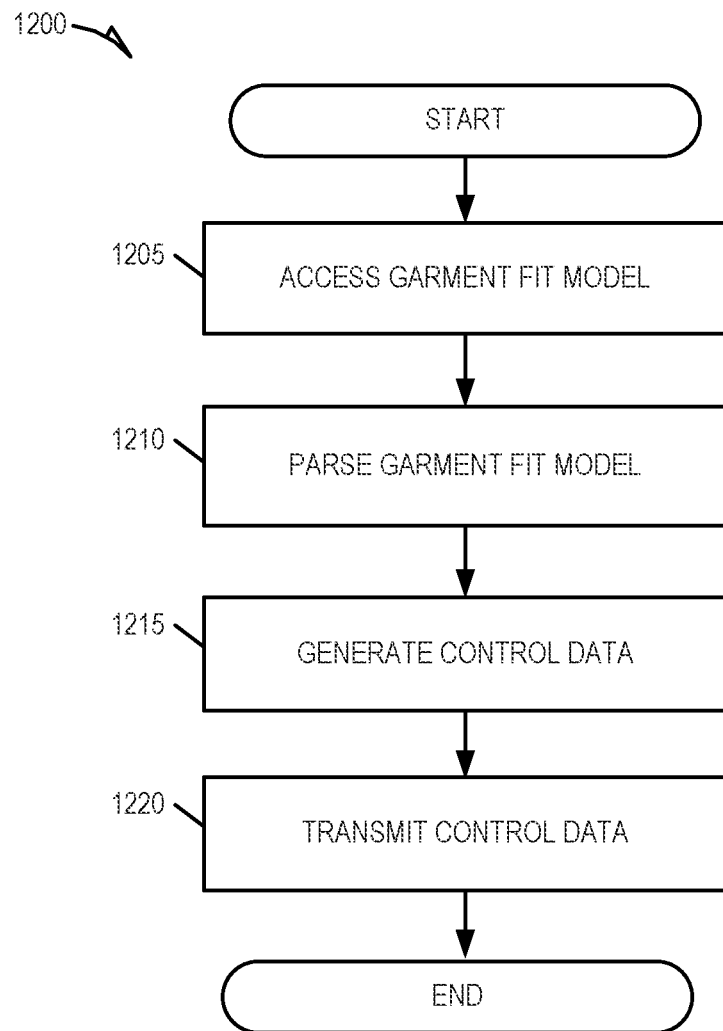
FIG. 12 is a flowchart illustrating a method for causing a fit simulation garment to simulate a garment fit on a human user, according to an example embodiment.

FIG. 12 is a flow diagram illustrating a method 1200 for causing the fit simulation garment 1002 to simulate a garment fit on the human user 106, according to an example embodiment. The method 1200 may be embodied in computer-readable instructions for execution by one or more processors such that the steps of the method 1200 may be performed in part or in whole by the controller 1004 and the receiver 1006. However, it shall be appreciated that the method 1200 may be deployed on various other hardware configurations and is not intended to be limited to the controller 1004 and the receiver 1006.

At operation 1205, the receiver 1006 receives a garment fit model (e.g., the garment fit model 110) that specifies the fit of a physical garment (e.g., the garment 114) on the human user 106. Consistent with some embodiments, the garment fit model may be obtained from a network-based marketplace or accessed from a networked database. The garment fit model may be accessed in response to or triggered by a request received from a client device of the human user 106 while browsing garments listed on or by a network-based marketplace.

At operation 1210, the controller 1004 parses the garment fit model to determine tightness of the various regions of the physical garment on the human user 106. For example, the controller 1004 may determine an amount of pressure (e.g., a forced applied over an area) applied by regions 116 of the garment 114 on the human user 106 based on information included in the garment fit model 110.

At operation 1215, the controller 1004 generates a set of control data based on the determined tightness of the various regions of the physical garment. At operation 1220, the controller 1004 transmits the control data to the fit simulation garment 1002 being worn by the human user 106. The controller 1004 may transmit the control data using a low energy transmission protocol such as BLE. In embodiments in which each actuator 1102 includes a respective wireless receiver 1006, the controller 1004 may transmit the control data as a plurality of control signals, with each control signal being specific to each actuator, and being transmitted to a corresponding receiver.

The control data, once received by the fit simulation garment 1002, causes the fit simulation garment 1002 to simulate the fit of the physical garment on the human user 106. In some embodiments, the control data may cause the plurality of actuators 1102 comprising the fit simulation garment 1002 to increase or decrease the tightness of various regions 116 of the fit simulation garment 1002. For example, the control data may cause at least a portion of the actuators 1102 to increase the tension on one or more tensioning bands 1104 comprising the fit simulation garment 1002. In another example, the control data may cause an actuator 1102 to inflate an inflatable air pocketed included in the fit simulation garment 1002.

Figure 13:
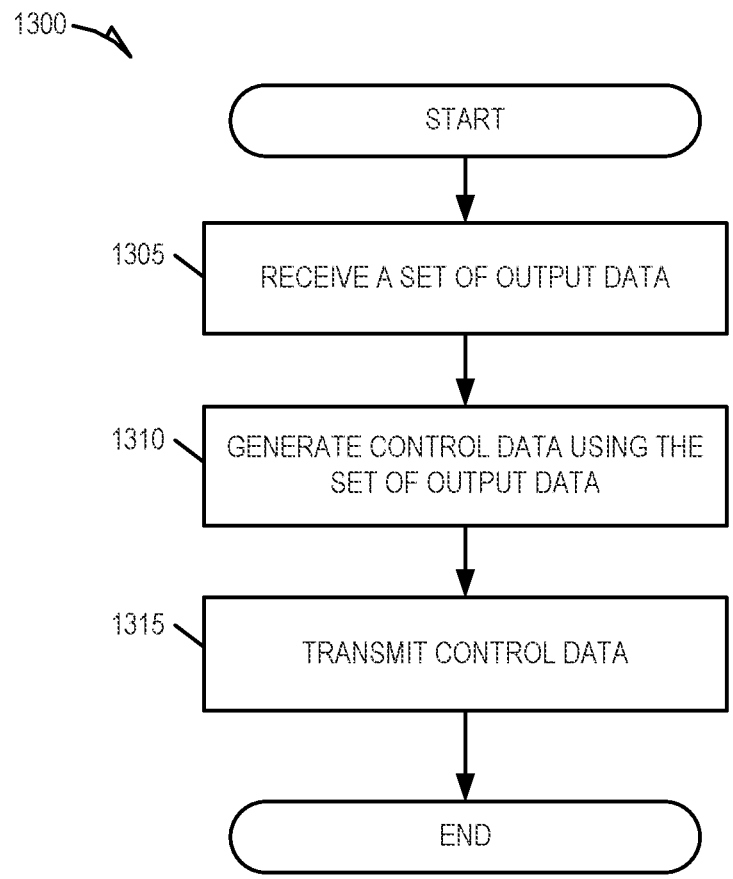
FIG. 13 is a flowchart illustrating a method for causing a fit simulation garment to simulate a garment fit on a human user, according to an alternative embodiment.

FIG. 13 is a flow diagram illustrating a method 1300 for causing the fit simulation garment 1002 to simulate a garment fit on the human user 106, according to an alternative embodiment. The method 1300 may be embodied in computer-readable instructions for execution by one or more processors such that the steps of the method 1300 may be performed in part or in whole by the controller 1004 and the receiver 1006. However, it shall be appreciated that the method 1300 may be deployed on various other hardware configurations and is not intended to be limited to the controller 1004 and the receiver 1006.

At operation 1305, the receiver 1006 receives output data from a personalized fitting mannequin 120. The output data received from the personalized fitting mannequin 120 corresponds to output of the plurality of sensors 122 comprising the personalized fitting mannequin 120. Respective output from each sensor 122 corresponds to the tightness of regions (e.g., regions 116) of the physical garment 114 on the personalized fitting mannequin 120. Because the personalized fitting mannequin 120 is designed to be metrologically correct representation of the human user 106, the output data produced by the personalized fitting mannequin 120 corresponds to the actual tightness of the garment 114 on the human user 106

At operation 1310, the controller 1004 generates a set of control data using the output data from the personalized fitting mannequin 120. For example, the controller 1004 may analyze the output data to determine an amount of pressure corresponding to a region of the physical garment 114, and in turn, the controller 1004 may generate a control signal to cause an actuator 1102 to exert the amount of pressure at a corresponding region of the fit simulation garment 1002.

At operation 1315, the controller 1004 transmits the control data to the fit simulation garment 1002 being worn by the human user 106. The controller 1004 may transmit the control data using a low energy transmission protocol such as BLE. In embodiments in which each actuator 1102 includes a respective wireless receiver 1006, the controller 1004 may transmit the control data as a plurality of control signals, with each control signal being specific to each actuator 1102, and being transmitted to a corresponding receiver.

The control data, once received by the fit simulation garment 1002, causes the fit simulation garment 1002 to simulate the fit of the physical garment 114 on the human user 106. In some embodiments, the control data may cause a plurality of actuators 1102 comprising the fit simulation garment 1002 to increase or decrease the tightness of various regions 1008 of the fit simulation garment 1002. For example, the control data may cause at least a portion of the actuators 1102 to increase the tension on one or more tensioning bands 1104 comprising the fit simulation garment 1002. In another example, the control data may cause an actuator 1102 to inflate an inflatable air pocketed included in the fit simulation garment 1002.

Figure 14:
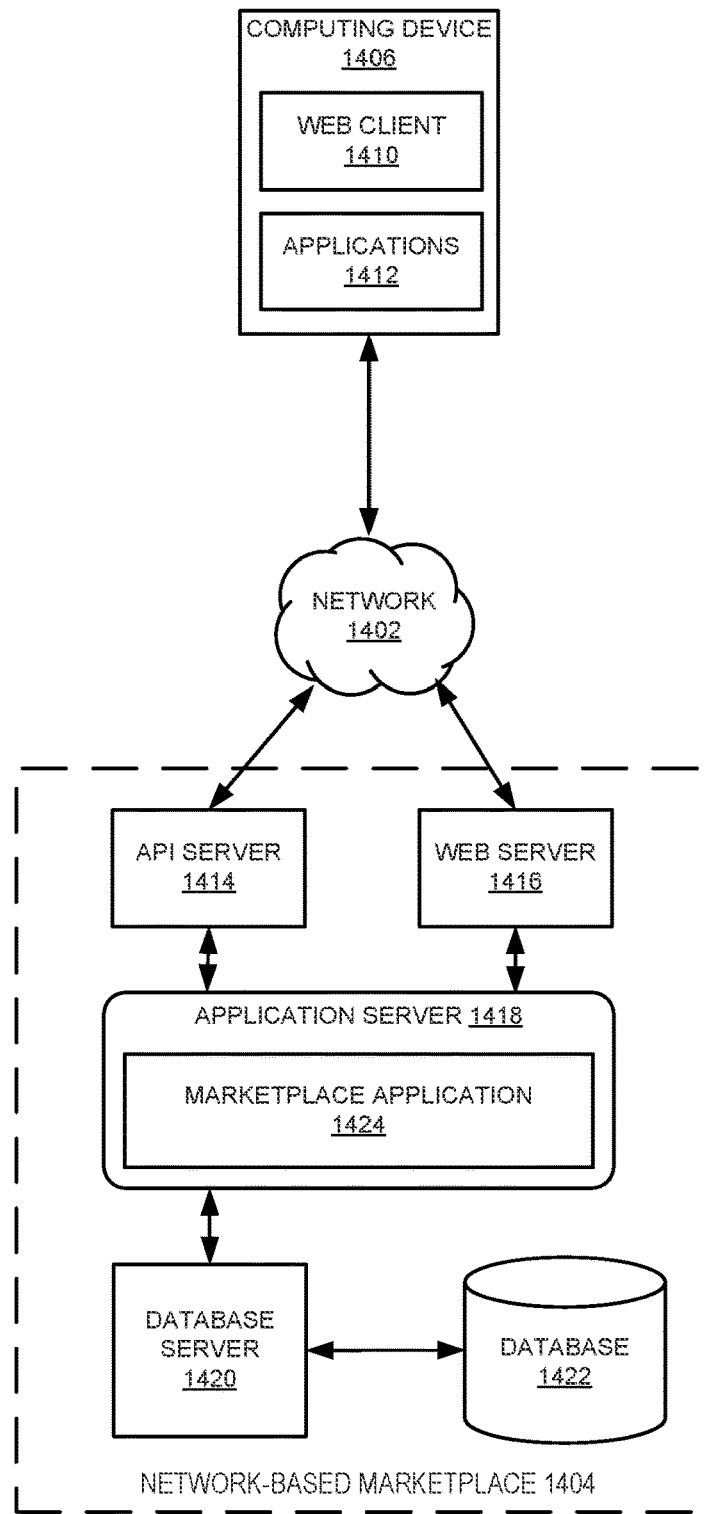
FIG. 14 is network diagram depicting a network system having a client-server architecture configured for exchanging data over a network with a network-based marketplace, according to an example embodiment.

FIG. 14 is network diagram depicting a network system 1400 having a client-server architecture configured for exchanging data over a network 1402 with a network-based marketplace 1404, according to an example embodiment. While the network system 1400 is depicted as having a client-server architecture, the present inventive subject matter is, of course, not limited to such an architecture, and could equally well find application in an event-driven, distributed, or peer-to-peer architecture system, for example. Further, to avoid obscuring the inventive subject matter with unnecessary detail, various functional components that are not germane to conveying an understanding of the inventive subject matter have been omitted from FIG. 14. Moreover, it shall be appreciated that although the various functional components of the network system 1400 are discussed in the singular sense, multiple instances of any one of the various functional components may be employed.

The network system 1400 may include the network-based marketplace 1404 in communication with a client device 1406. The network-based marketplace 1404 may communicate and exchange data within the network system 1400 that may pertain to various functions and aspects associated with the network system 1400 and its users 106. The network-based marketplace 1404 may provide server-side functionality, via a network 1402 (e.g., the Internet), to network devices such as the client device 1406.

The client device 1406 may be operated by users (e.g., the human user 106) who use the network system 1400 to exchange data over the network 1402. These data exchanges may include transmitting, receiving (communicating), and processing data to, from, and regarding content and users of the network system 1400. The data may include, but are not limited to output data from sensors; command data; body shape models; garment models; garment wear models; garment fit models; images; video or audio content; user preferences; product and service feedback, advice, and reviews; product, service, manufacturer, and vendor recommendations and identifiers; product and service listings associated with buyers and sellers; product and service advertisements; auction bids; transaction data; user profile data; and social data, among other things.

The client device 1406 may interface with the network-based marketplace 1404 via a connection with the network 1402. In some embodiments, the client device 1406 may correspond to the computing device 108 and may be in communication with any one of the body measurement garment 104, the personalized fit mannequin 120, and the fit simulation garment 1002 (e.g., via the network 1402).

Depending on the form of the client device 1406, any of a variety of types of connections and networks 1402 may be used. For example, the connection may be Code Division Multiple Access (CDMA) connection, a Global System for Mobile communications (GSM) connection, or another type of cellular connection. Such a connection may implement any of a variety of types of data transfer technology, such as Single Carrier Radio Transmission Technology (1×RTT), Evolution-Data Optimized (EVDO) technology, General Packet Radio Service (GPRS) technology, Enhanced Data rates for GSM Evolution (EDGE) technology, or other data transfer technology (e.g., fourth generation wireless, 4G networks). When such technology is employed, the network 1402 may include a cellular network that has a plurality of cell sites of overlapping geographic coverage, interconnected by cellular telephone exchanges. These cellular telephone exchanges may be coupled to a network backbone (e.g., the public switched telephone network (PSTN), a packet-switched data network, or other types of networks).

In another example, the connection to the network 1402 may be a Wireless Fidelity (Wi-Fi, IEEE 802.11x type) connection, a Worldwide Interoperability for Microwave Access (WiMAX) connection, or another type of wireless data connection. In such an embodiment, the network 1402 may include one or more wireless access points coupled to a local area network (LAN), a wide area network (WAN), the Internet, or another packet-switched data network. In yet another example, the connection to the network 1402 may be a wired connection (e.g., an Ethernet link), and the network 1402 may be a LAN, a WAN, the Internet, or another packet-switched data network. Accordingly, a variety of different configurations are expressly contemplated.

In various embodiments, the data exchanged within the network system 1400 may be dependent upon user-selected functions available through one or more client or user interfaces (UIs). The UIs may be associated with a client device, such as the client device 1406 executing a web client 1410 (e.g., an Internet browser), which may be in communication with the network-based marketplace 1404. The UIs may also be associated with one or more applications 1412 executing on the client device 1406, such as a mobile application designed for interacting with the network-based marketplace 1404. For example, in some embodiments, the client device 1406 may be executing the body measurement application 500.

Turning specifically to the network-based marketplace 1404, an API server 1414 and a web server 1416 are coupled to, and provide programmatic and web interfaces respectively to, an application server 1418. As illustrated in FIG. 14, the application server 1418 may be coupled via the API server 1414 and the web server 1416 to the network 1402, for example, via wired or wireless interfaces. The application server 1418 is, in turn, shown to be coupled to a database server 1420 that facilitates access to a database 1422. In some examples, the application server 1418 can access the database 1422 directly without the need for the database server 1420. The database 1422 may include multiple databases that may be internal or external to the network-based marketplace 1404.

The application server 1418 may, for example, host one or more applications, which may provide a number of content publishing and viewing functions and services to users 106 who access the network-based marketplace 1404. For example, in some embodiments, the application server 1418 corresponds to the computing device 108 and hosts body measurement application 500 that provides a number of body measurement and modeling services to users 106 of the networked system 1400. As illustrated in FIG. 14, the network-based marketplace 1404 hosts a marketplace application 1424 that provides a number of marketplace functions and services to users 106, such as publishing, listing, and price-setting mechanisms whereby a seller may list (or publish information concerning) goods or services (also collectively referred to as "products") for sale, a buyer can express interest in or indicate a desire to purchase such goods or services, and a price can be set for a transaction pertaining to the goods or services.

The database 1422 stores data pertaining to various functions and aspects associated with the network system 1400 and its users 106. For example, the database 1422 may include a repository of garment models 110 describing various aspects (e.g., dimensions, fabric type, and tensile strength of fabric) of real-world physical garments 114. The database 1422 may store and maintain user profiles for users 106 of the network-based marketplace 1404. Each user profile may comprise user profile data that describes aspects of a particular user 106. The user profile data may, for example, include a measurement profile, a body shape model 102, demographic data, user preferences, social data (e.g., information obtained from one or more social network platforms), and financial information. The demographic data may, for example, include information describing one or more characteristics of a user 106 such as gender, age, location information (e.g., hometown or current location), employment history, education history, contact information, familial relations, or user interests. The financial information may, for example, include private financial information of the user 106 such as account number, credential, password, device identifier, user name, phone number, credit card information, bank information, transaction history, or other financial information which may be used to facilitate online transactions by the user 106.

Modules, Components and Logic

Certain embodiments are described herein as including logic or a number of components, modules, or mechanisms. Modules may constitute either software modules (e.g., code embodied on a machine-readable medium or in a transmission signal) or hardware modules. A hardware module is a tangible unit capable of performing certain operations and may be configured or arranged in a certain manner. In example embodiments, one or more computer systems (e.g., a standalone, client, or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field-programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner and/or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses that connect the hardware modules). In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods described herein may be at least partially processor-implemented. For example, at least some of the operations of a method may be performed by one or more processors or processor-implemented modules. The performance of certain of the operations may be distributed among the one or more processors, not only residing within a single machine, but deployed across a number of machines. In some example embodiments, the processor or processors may be located in a single location (e.g., within a home environment, an office environment, or a server farm), while in other embodiments the processors may be distributed across a number of locations.

The one or more processors may also operate to support performance of the relevant operations in a "cloud computing" environment or as a "software as a service" (SaaS). For example, at least some of the operations may be performed by a group of computers (as examples of machines including processors), with these operations being accessible via a network 1402 (e.g., the Internet) and via one or more appropriate interfaces (e.g., APIs).

Electronic Apparatus and System

Example embodiments may be implemented in digital electronic circuitry, or in computer hardware, firmware, or software, or in combinations of them. Example embodiments may be implemented using a computer program product, for example, a computer program tangibly embodied in an information carrier, for example, in a machine-readable medium for execution by, or to control the operation of, data processing apparatus, for example, a programmable processor, a computer, or multiple computers.

A computer program can be written in any form of programming language, including compiled or interpreted languages, and it can be deployed in any form, including as a standalone program or as a module, subroutine, or other unit suitable for use in a computing environment. A computer program can be deployed to be executed on one computer or on multiple computers at one site, or distributed across multiple sites and interconnected by a communication network 1402.

In example embodiments, operations may be performed by one or more programmable processors executing a computer program to perform functions by operating on input data and generating output. Method operations can also be performed by, and apparatus of example embodiments may be implemented as, special purpose logic circuitry (e.g., an FPGA or an ASIC).

The computing system can include clients and servers. A client and server are generally remote from each other and typically interact through a communication network 1402. The relationship of client and server arises by virtue of computer programs running on the respective computers and having a client-server relationship to each other. In embodiments deploying a programmable computing system, it will be appreciated that both hardware and software architectures merit consideration. Specifically, it will be appreciated that the choice of whether to implement certain functionality in permanently configured hardware (e.g., an ASIC), in temporarily configured hardware (e.g., a combination of software and a programmable processor), or in a combination of permanently and temporarily configured hardware may be a design choice. Below are set out hardware (e.g., machine) and software architectures that may be deployed, in various example embodiments.

Machine Architecture

Figure 15:
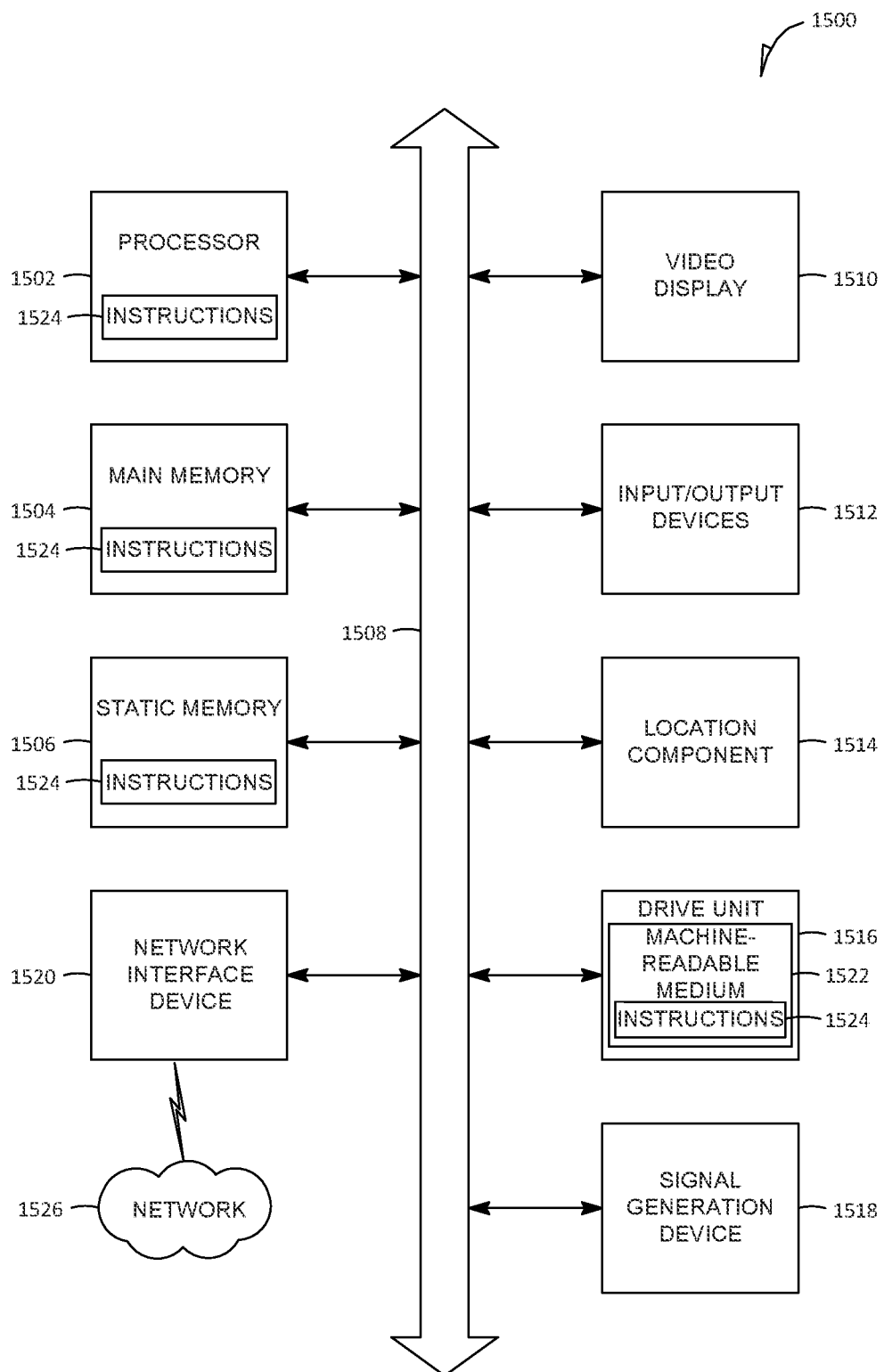
FIG. 15 is a diagrammatic representation of a machine in the example form of a computer system within which a set of instructions for causing the machine to perform any one or more of the methodologies discussed herein may be executed.

FIG. 15 is a diagrammatic representation of a machine in the example form of a computer system 1500 within which a set of instructions for causing the machine to perform any one or more of the methodologies discussed herein may be executed. The computer system 1500 may correspond to the computing device 108, the client device 1406, the API server 1414, the web server 1416, or the application server 1418, consistent with some embodiments. The computer system 1500 may include instructions for causing the machine to perform any one or more of the methodologies discussed herein. In alternative embodiments, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a personal computer (PC), a personal digital assistant (PDA), a cellular telephone, a smart phone (e.g., iPhone®), a tablet computer, a web appliance, a handheld computer, a desktop computer, a laptop or netbook, a set-top box (STB) such as those provided by cable or satellite content providers, a wearable computing device such as glasses or a wristwatch, a multimedia device embedded in an automobile, a Global Positioning System (GPS) device, a data enabled book reader, a video game system console, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 1500 includes a processor 1502 (e.g., a central processing unit (CPU), a graphics processing unit (GPU), or both), a main memory 1504, and a static memory 1506, which communicate with each other via a bus 1508. The computer system 1500 may further include a video display 1510 (e.g., a liquid crystal display (LCD) or a cathode ray tube (CRT)). The computer system 1500 also includes one or more input/output (I/O) devices 1512, a location component 1514, a drive unit 1516, a signal generation device 1518 (e.g., a speaker), and a network interface device 1520. The I/O devices 1512 may, for example, include a keyboard, a mouse, a keypad, a multi-touch surface (e.g., a touchscreen or track pad), a microphone, a camera, and the like.

The location component 1514 may be used for determining a location of the computer system 1500. In some embodiments, the location component 1514 may correspond to a GPS transceiver that may make use of the network interface device 1520 to communicate GPS signals with a GPS satellite. The location component 1514 may also be configured to determine a location of the computer system 1500 by using an Internet Protocol (IP) address lookup or by triangulating a position based on nearby mobile communications towers. The location component 1514 may be further configured to store a user-defined location in the main memory 1504 or the static memory 1506. In some embodiments, a mobile location enabled application may work in conjunction with the location component 1514 and the network interface device 1520 to transmit the location of the computer system 1500 to an application server 1418 or third party server for the purpose of identifying the location of a user 106 operating the computer system 1500.

In some embodiments, the network interface device 1520 may correspond to a transceiver and antenna. The transceiver may be configured to both transmit and receive cellular network signals, wireless data signals, or other types of signals via the antenna, depending on the nature of the computer system 1500.

Machine-Readable Medium

The drive unit 1516 includes a machine-readable medium 1522 on which is stored one or more sets of data structures and instructions 1524 (e.g., software) embodying or used by any one or more of the methodologies or functions described herein. The instructions 1524 may also reside, completely or at least partially, within the main memory 1504, the static memory 1506, and/or the processor 1502 during execution thereof by the computer system 1500, with the main memory 1504, the static memory 1506, and the processor 1502 also constituting machine-readable media 1522.

Consistent with some embodiments, the instructions 1524 may relate to the operations of an operating system (OS). Depending on the particular type of the computer system 1500, the OS may, for example, be the iOS® operating system, the Android® operating system, a BlackBerry® operating system, the Microsoft® Windows® Phone operating system, Symbian® OS, or webOS®. Further, the instructions 1524 may relate to operations performed by applications (commonly known as "apps"), consistent with some embodiments. One example of such an application is a mobile browser application that displays content, such as a web page or a user interface using a browser.

While the machine-readable medium 1522 is shown in an example embodiment to be a single medium, the term "machine-readable medium" may include a single medium or multiple media (e.g., a centralized or distributed database, and/or associated caches and servers) that store the one or more data structures or instructions 1524. The term "machine-readable medium" shall also be taken to include any tangible medium that is capable of storing, encoding, or carrying instructions (e.g., the instructions 1524) for execution by the machine and that cause the machine to perform any one or more of the methodologies of the present disclosure, or that is capable of storing, encoding, or carrying data structures used by or associated with such instructions. The term "machine-readable medium" shall accordingly be taken to include, but not be limited to, solid-state memories, and optical and magnetic media. Specific examples of machine-readable media include non-volatile memory, including by way of example semiconductor memory devices (e.g., erasable programmable read-only memory (EPROM), electrically erasable programmable read-only memory (EEPROM)) and flash memory devices; magnetic disks such as internal hard disks and removable disks; magneto-optical disks; and CD-ROM and DVD-ROM disks.

Furthermore, the tangible machine-readable medium is non-transitory in that it does not embody a propagating signal. However, labeling the tangible machine-readable medium "non-transitory" should not be construed to mean that the medium is incapable of movement—the medium should be considered as being transportable from one real-world location to another. Additionally, since the machine-readable medium is tangible, the medium may be considered to be a machine-readable device.

Transmission Medium

The instructions 1524 may further be transmitted or received over a network 1526 using a transmission medium. The instructions 1524 may be transmitted using the network interface device 1520 and any one of a number of well-known transfer protocols (e.g., HTTP). Examples of communication networks include a LAN, a WAN, the Internet, mobile telephone networks, POTS networks, and wireless data networks (e.g., WiFi and WiMax networks). The term "transmission medium" shall be taken to include any intangible medium that is capable of storing, encoding, or carrying the instructions 1524 for execution by the machine, and includes digital or analog communications signals or other intangible media to facilitate communication of such software.

Although the embodiments of the present inventive subject matter have been described with reference to specific example embodiments, it will be evident that various modifications and changes may be made to these embodiments without departing from the broader scope of the inventive subject matter. Accordingly, the specification and drawings are to be regarded in an illustrative rather than a restrictive sense. The accompanying drawings that form a part hereof show by way of illustration, and not of limitation, specific embodiments in which the subject matter may be practiced. The embodiments illustrated are described in sufficient detail to enable those skilled in the art to practice the teachings disclosed herein. Other embodiments may be used and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

All publications, patents, and patent documents referred to in this document are incorporated by reference herein in their entirety, as though individually incorporated by reference. In the event of inconsistent usages between this document and those documents so incorporated by reference, the usage in the incorporated references should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended; that is, a system, device, article, or process that includes elements in addition to those listed after such a term in a claim are still deemed to fall within the scope of that claim. Moreover, in the following claims, the terms "first," "second," "third," and so forth are used merely as labels, and are not intended to impose numerical requirements on their objects.

What is claimed is:

1. A method comprising:
receiving information measured by a plurality of embedded sensors of a body measurement garment worn by a user, the information including an amount of pressure exerted by the body measurement garment on the user measured by the plurality of embedded sensors of the body measurement garment;
determining a tightness of a plurality of different regions of the body measurement garment worn by the user based on the information measured by the plurality of embedded sensors of the body measurement garment worn by the user, wherein the tightness is determined from the amount of pressure exerted by the body measurement garment on the user measured by the plurality of embedded sensors of the body measurement garment; and generating a garment fit model based on the tightness of the plurality of different regions of the body measurement garment worn by the user.

2. The method of claim 1, wherein the tightness corresponds to an amount of pressure exerted by the body measurement garment on the user at the plurality of different regions.

3. The method of claim 1, wherein the tightness includes an indication of one or more of the plurality of different regions of the body measurement garment that exceed a predefined threshold for tightness.

4. The method of claim 1, wherein the tightness includes an indication of one or more of the plurality of different regions of the body measurement garment that are below a predefined threshold for looseness.

5. The method of claim 1, further comprising:
rendering, by a computing device, the garment fit model to present a three-dimensional visual representation of the garment being worn by the user; and
causing one or more or the plurality of different regions of the body measurement garment which are above a predefined threshold for tightness to be visually distinguished on the garment fit model displayed on the display of the computing device.

6. The method of claim 1, further comprising:
rendering, by a computing device, the garment fit model to present a three-dimensional visual representation of the garment being worn by the user; and
causing one or more or the plurality of different regions of the body measurement garment which are below a predefined threshold for looseness to be visually distinguished on the garment fit model displayed on the display of the computing device.

7. The method of claim 1, further comprising:
rendering, by a computing device, the garment fit model to present a three-dimensional visual representation of the garment being worn by the user; and
causing one or more or the plurality of different regions of the body measurement garment which are above a predefined threshold for tightness to be visually distinguished on the garment fit model displayed on the display of the computing device; and
causing one or more or the plurality of different regions of the body measurement garment which are below a predefined threshold for looseness to be visually distinguished on the garment fit model displayed on the display of the computing device.

8. A tangible machine-readable storage medium embodying instructions that, when executed by a machine, cause the machine to perform operations comprising:
receiving information measured by a plurality of embedded sensors of a body measurement garment worn by a user, the information including an amount of pressure exerted by the body measurement garment on the user measured by the plurality of embedded sensors of the body measurement garment;
determining a tightness of a plurality of different regions of the body measurement garment worn by the user based on the information measured by the plurality of embedded sensors of the body measurement garment worn by the user, wherein the tightness is determined from the amount of pressure exerted by the body measurement garment on the user measured by the plurality of embedded sensors of the body measurement garment; and
generating a garment fit model based on the tightness of the plurality of different regions of the body measurement garment worn by the user.

9. The tangible machine-readable storage medium of claim 8, wherein the tightness corresponds to an amount of pressure exerted by the body measurement garment on the user at the plurality of different regions.

10. The tangible machine-readable storage medium of claim 8, wherein the tightness includes an indication of one or more of the plurality of different regions of the body measurement garment that exceed a predefined threshold for tightness.

11. The tangible machine-readable storage medium of claim 8, wherein the tightness includes an indication of one or more of the plurality of different regions of the body measurement garment that are below a predefined threshold for looseness.

12. The tangible machine-readable storage medium of claim 8, wherein the operations further comprise:
rendering, on a display of a computing device, the garment fit model to present a three-dimensional virtual representation of the garment being worn by the user;
causing one or more or the plurality of different regions of the body measurement garment which are above a predefined threshold for tightness to be visually distinguished on the garment fit model displayed on the display of the computing device; and
causing one or more or the plurality of different regions of the body measurement garment which are below a predefined threshold for looseness to be visually distinguished on the garment fit model displayed on the display of the computing device.

13. A system comprising:
a body measurement garment comprising a plurality of sensors to generate outputs corresponding to measurements of a user wearing the body measurement garment; and
a computing device configured to obtain the outputs and generate a garment fit model based on the outputs and render the garment fit model to present a three-dimensional virtual representation of the garment being worn by the user.

14. The system of claim 13, wherein the outputs correspond to a tightness of the body measurement garment on the user.

15. The system of claim 14, wherein the tightness corresponds to an amount of pressure exerted by the body measurement garment on the user at a plurality of different regions of the body measurement garment worn by the user, each of the plurality of different regions corresponding to one of the plurality of sensors.

16. The system of claim 15, wherein the tightness includes an indication of one or more of the plurality of different regions of the body measurement garment that exceed a predefined threshold for tightness.

17. The system of claim 16, wherein the tightness includes an indication of one or more of the plurality of different regions of the body measurement garment that are below a predefined threshold for looseness.

18. The system of claim 13, wherein the outputs correspond to a looseness of the body measurement garment on the user.

19. The method of claim 1, wherein each of the plurality of different regions correspond to one of the plurality of embedded sensors.

20. The tangible machine-readable storage medium of claim 8, wherein each of the plurality of different regions correspond to one of the plurality of embedded sensors.

* * * * *